US010426826B2

(12) United States Patent
Kim et al.

(10) Patent No.: US 10,426,826 B2
(45) Date of Patent: Oct. 1, 2019

(54) VACCINE COMPOSITION FOR TREATING OR PREVENTING SHIGELLOSIS

(71) Applicant: International Vaccine institute, Seoul (KR)

(72) Inventors: Jae Ouk Kim, Seoul (KR); Min Jung Kim, Seoul (KR); Man Ki Song, Seoul (KR)

(73) Assignee: International Vaccine Institute, Seoul (KR)

( * ) Notice: Subject to any disclaimer, the term of this patent is extended or adjusted under 35 U.S.C. 154(b) by 0 days.

(21) Appl. No.: 15/569,055

(22) PCT Filed: Apr. 22, 2016

(86) PCT No.: PCT/KR2016/004264
§ 371 (c)(1),
(2) Date: Oct. 24, 2017

(87) PCT Pub. No.: WO2016/171524
PCT Pub. Date: Oct. 27, 2016

(65) Prior Publication Data

US 2018/0133300 A1 May 17, 2018

Related U.S. Application Data

(60) Provisional application No. 62/152,221, filed on Apr. 24, 2015.

(51) Int. Cl.

| | |
|---|---|
| ***A61K 45/00*** | (2006.01) |
| ***A61K 39/00*** | (2006.01) |
| ***C07H 21/04*** | (2006.01) |
| ***A61K 39/112*** | (2006.01) |
| ***A61K 39/39*** | (2006.01) |
| ***C12N 1/20*** | (2006.01) |
| ***A61P 31/04*** | (2006.01) |
| ***C12N 1/36*** | (2006.01) |
| ***C12N 9/10*** | (2006.01) |

(52) U.S. Cl.
CPC .......... *A61K 39/0283* (2013.01); *A61K 39/39* (2013.01); *A61P 31/04* (2018.01); *C12N 1/20* (2013.01); *C12N 1/36* (2013.01); *C12N 9/1081* (2013.01); *A61K 2039/521* (2013.01); *A61K 2039/522* (2013.01); *A61K 2039/54* (2013.01); *A61K 2039/541* (2013.01); *A61K 2039/542* (2013.01); *A61K 2039/543* (2013.01); *A61K 2039/575* (2013.01)

(58) Field of Classification Search
CPC ..... A61K 39/00; A61K 39/02; A61K 39/0283
USPC ... 424/93.1, 93.2, 93.4, 184.1, 185.1, 234.1, 424/278.1
See application file for complete search history.

(56) References Cited

U.S. PATENT DOCUMENTS

| | | | |
|---|---|---|---|
| 8,147,847 | B2 | 4/2012 | Czerkinsky et al. |
| 2010/0272748 | A1 | 10/2010 | Kopecko et al. |

FOREIGN PATENT DOCUMENTS

| | | | | |
|---|---|---|---|---|
| WO | WO 2010/046778 A2 | 4/2010 | | |
| WO | WO2014/037440 A2 * | 3/2014 | ............ A61K 39/02 | |
| WO | WO 2014/037440 A2 | 3/2014 | | |

OTHER PUBLICATIONS

Daniels, C., et al., Molecular Microbiology, vol. 28, No. 6, pp. 1211-1222, 1998.*

Daniels, Craig, et al., "Overexpression and Topology of the *Shigella flexneri* O-Antigen Polymerase (Rfc/Wzy)", Molecular Microbiology, v. 28, No. 6, p. 1211-1222, 1998.

Kim, Dong Wook, et al., "The *Shigella flexneri* Effector OspG Interferes with Innate Immune Responses by Targeting Ubiquitin-Conjugating Enzymes", PNAS, v. 102, No. 39, p. 14046-14051, Sep. 27, 2005.

Kim, Jae-Ouk, et al., "*Shigella* Outer Membrane Protein PSS-1 is Broadly Protective Against *Shigella* Infection", Clinical and Vaccine Immunology, v. 22, No. 4, p. 381-388, Apr. 2015.

Kong, Qingke, et al., "Effect of Deletion of Genes Involved in Lipopolysaccharide Core and O-Antigen Synthesis on Virulence and Immunogenicity of *Salmonella enterica* Serovar Typhimurium", Infection and Immunity, v. 79, No. 10, p. 4227-4239, Oct. 2011.

Liu, B., et al., "Structure and Genetics of Shigella O Antigens", GenBank Accession No. EU296404, Aug. 26, 2008.

Norton, Elizabeth B., et al., "Characterization of a Mutant *Escherichia coli* Heat-Labile Toxin, LT(R192/L211A), as a Safe and Effective Oral Adjuvant", Clinical and Vaccine Immunology, v. 18, No. 4, p. 546-551, Apr. 2011.

* cited by examiner

*Primary Examiner* — Rodney P Swartz
(74) *Attorney, Agent, or Firm* — Morgan, Lewis & Bockius LLP

(57) ABSTRACT

The present invention relates to a *Shigella* strain, of which the surface exposure of a protective antigen existing on a cellular membrane is increased due to the destruction of a wzy gene of *Shigella* sp., and to a vaccine composition for treating or preventing shigellosis, containing the mutant *Shigella* strain as an active ingredient. The *Shigella* strain of the present invention has a cell wall with a reduced thickness since a gene encoding a protein necessary for polymerization of the O-saccharide antigen is deleted, and as a result, membrane antigens including protein antigens commonly existing in different *Shigella* spp. are more exposed to immune cells, and thus the *Shigella* strain can be favorably used as a vaccine composition for treating or preventing shigellosis, derived from various *Shigella* spp.

10 Claims, 17 Drawing Sheets

Specification includes a Sequence Listing.

SEQUENCE LISTING

```
<160> NUMBER OF SEQ ID NOS: 17

<210> SEQ ID NO 1
<211> LENGTH: 1149
<212> TYPE: DNA
<213> ORGANISM: Shigella flexneri 2a
```

<400> SEQUENCE: 1

```
atgaataata taaataaaat ttttataaca tttttatgta ttgaactgat tattggtggt     60
ggtggaagat tactggagcc attgggaata ttccctttgc gatatttatt atttgtattt    120
agttttatac ttttaatttt taatttagtt acattcaatt tttcaatcac ccaaaaatgt    180
gtcagtcttt ttatatggtt gcttttattt cctttttatg gcttctttgt cggcttatta    240
gctggtaata aaataaatga tatactgttt gatgtgcaac catacctttt tatgctgtca    300
cttatatatc tatttacact aagatatact ttaaaagtat tttcatgtga gatttttatt    360
aaaatagtta atgcatttgc attatatgga tcactgttat atatttcata cataattttg    420
ttgaatttcg gtttgttaaa ttttaattta atttatgaac acttatcatt gactagcgag    480
ttcttttttc gtcccgatgg ggcttttttt tccaaatcct tctacttttt tggtgtcggt    540
gcgattatca gttttgtcga caaaaaatat ttaaaatgtc tcataatagt gcttgcgata    600
ttattgacag aatcaagagg tgtattactt tttacaacat tatcactgtt attagccagt    660
tttaaattac ataagctata tttaaatact attataataa tattgggcag cgttctattt    720
ataattatgc tttacatggt cggatcacgc agtgaagatt ctgactctgt tagatttaat    780
gatttatatt tttattataa aaatgttgat ttagcgacgt tcttgtttgg aagaggattt    840
ggttcattta tattagatcg attaaggatt gaaatagtac ctcttgagat acttcagaaa    900
acaggcgtta ttggtgtatt tatatcatta gttcctatgt tgcttatctt tttgaaaggc    960
tatttttttaa atagtacaaa aacatcatta atgatgtcgt taatactttt tttcagtatt   1020
accgtttcta taactaatcc atttcttttt acacccatgg gaatttttat tataggcgtt   1080
gtagttttat gggtattttc tatagaaaat atccaaatta gtaataacct cacttctgga   1140
gcaaaataa                                                            1149
```

<210> SEQ ID NO 2
<211> LENGTH: 1188
<212> TYPE: DNA
<213> ORGANISM: Shigella flexneri 6

<400> SEQUENCE: 2

```
atgacttctg atttttataa ctcaaaagac aaaagtttaa gtgttctttt gttttttggg     60
tttatatttt tccttacacg tagctttcca tttattcaat atagttggat tatggagggg    120
tttttatgtc tttgtatcat gtcatttaca aagaaaattg caaacggaat atatcactat    180
cctgttattt taatatttct attagctctt tttataaatt ttatttattc ctatatcaag    240
ggtaacgata tagcgataat aattaggttt tatattatca tattatttat attatgtgct    300
tatttctgct cttatggaac catctcgatt gttaaaatat ttttatattt aatggtatta    360
caggcggtta ttatatccat cattagtatt tatatgacaa aaacatatgg tattggtgat    420
tattcagcac taagacatta ttttttggag aatgattatg gtgatgttta tacatatgga    480
agtggtttct atagagttca aattaaagga aatgctctca ttccatttgc ctttatgttg    540
catatagtca taaaagatta tttctattat cgattcaaaa atacaataac cgttattctg    600
gctataggta ctatagtggc tggtaatttt gcatattttg tttcgatatg cttgtttttt    660
atgtatatta tactatgttc taaatctaac tcacgatacg ctaaattaag gaaaattatt    720
tttggggttt ttcttactgt gattctccct tttttttatta catattcaat tgagttgata    780
atcatgaaat caaatggagc tgattcttct ttaggagtta gatgggatca gtttactgta    840
```

-continued

```
ttaattaatg atcttacaga gtctgtatca aattttgtta taggttctgg tttgggtaat    900

gtcatcaaaa ttcaaactcc tatccgtgat tatagtgcat atatatatta tgaattgcag    960

tcagtttatt ttttaaatca acttggcgtt attttattta ctttgttttt attaattaat   1020

ctccttctca cgattaaaat cataaaatac agtgagttgt gtgtgctata ttttctatat   1080

gtttcttatg caattactaa tccttatatt ttagactcta accatgttgc tgtaataatt   1140

gtattagtga cattaagtaa tgttctaaaa aagatgaaag ctaaatga                1188
```

```
<210> SEQ ID NO 3
<211> LENGTH: 1086
<212> TYPE: DNA
<213> ORGANISM: Shigella dysenteriae 2

<400> SEQUENCE: 3

atgataaaaa aaaataatat ttatagattt tatattttag tatgtgtatt tagtggtttt     60

tatatatttg gattctttcc tgccccatac tatctttgtt taatattggg gtttgtgttt    120

ttaagcctta gcaaaatcaa acatgttgat aaaaatattt tatttctgtt atgcattgtt    180

attatctata tggtttttat gttgtttaac tctagaatta atgtttggag ttattatttt    240

attggccttc tgacttattt tattattatc ttactaagaa ataatcttga taattatcaa    300

aaaattgcaa ttgtgagaaa gactgtctta atctcattgt tacttgtcat attggatact    360

atatatagat tctattatcc gcgagaagaa tatttacttg caatagaaca acaagggaaa    420

attgattatc tcttttatgg atataaacat agctttttat tccaagacag taatttcgta    480

ggtttatata ttttgtcagt ttttttttctg tttagggata acatgtctat ctttaaatgg    540

aaaaaaagta tcctattgac aataataata ttaattattt tatccttatc aagggcggca    600

atagtcgcat tgattttaac cgaatgtata cgtatgttat gtggcatgaa agttgatgta    660

cgattgaaaa ttgtgtcatt aatatttatg gccataccga caatatatct cttatttgtt    720

ttggtagcta atattgatga cacaagtttt gaatcgaaat tcatgctatt aaataaattt    780

cttactactt ttcaagaaag aaattttact gaattattat ttggatgggg cttagataat    840

acacgagaac actggggaat agctgctcat agtttattta atacattact tctggaaatg    900

ggattggtgg gattcattat aattaccata tcaatagtat attgttggtg cttaaacacc    960

aaaacgttat atcattttat ggggttaagc atagcatttc tttcatttgg tttgattttt   1020

actccatttt ttattcctct tggcttaaat ataattatgc gagatgtgtc gaatgaaaaa   1080

ctatga                                                              1086
```

```
<210> SEQ ID NO 4
<211> LENGTH: 1173
<212> TYPE: DNA
<213> ORGANISM: Shigella sonnei 482-79

<400> SEQUENCE: 4

atgttaatat acctatatcc tgtacttttg ttatttaata tccttccggt tttttttttat     60

ggacaaatga actctgattt agagcgtttt tttggagttc ctattggcta tattccagat    120

ctaatatttt atttctttgt tgttttaaca tctataataa cgttgaggtt tcacgtttct    180

ctgtggacaa agaaattatt atttttaggc atcatattcc tgatttatat cagcattcag    240

atgttgttgt tatcagcgga tatatcaggt gtcgtaattt tattatcgtt tttttctaat    300

tttatagctt tggttctttt ggtgtcattt tgcattggta aagatgagct ttatttaact    360

cattcggtta gaaatataaa tgttgtaatg tgttttggta ttatctgtgg agttgtaaaa    420
```

ttatttattg gttattctga agatagtaat tttatagttt atttaaatag aaatgccacc 480
gcaattatag tagtgtgctt ttattgtgta tattcatact tttatcgtgg tcgaaagtct 540
tggtatgtct catctgtatt gtactctctg ttctttcttt ttctggatag ccgagcagga 600
ataatatcat ttgctatatc gttgtttttt gtttttcttc agttaacaaa gaaggaaaag 660
ttattaatat cattgttttt tgttcctctt ctaactttag gtatttcttt tactgatata 720
ggcactcgtc ttgaacgaat gctgtcttcg tcacaggtta tattctctgg tggtaacact 780
cttacaaaaa gtcagaatga ttatcgtcga gttgagttag tatttattgg ggttgatgtt 840
ttaaaagaaa attatttaat tggcactgga ttaggtgttg caaattatgt aaaggctata 900
gataaaaagt ttttaggaag taccaacttt gggttggcgc ataattttta tttatcttat 960
tcggctcagt tagggattat tggtttttatt ttgcttattt ctgtatttta tataatgctg 1020
tctccaattt ttaaatgcgg agggtatatt ggtaaaggat gcgtttttgc tttggctttc 1080
tatgtctttt ttaatgagta tatattgacg ccagcgatat atatttatat ttctattttt 1140
ttatcggtgg tttttatacg taattctaaa tag 1173

<210> SEQ ID NO 5
<211> LENGTH: 1296
<212> TYPE: DNA
<213> ORGANISM: Shigella boydii 7

<400> SEQUENCE: 5
atgactaata taacgttcag aactctgaga attccaggat atttactctc attatttgtt 60
cttttaatcg gatttataac atatttcatc tttaatgaaa ctcttgcagc gaatttatta 120
gcagtggggg ctattggcat tatcattctt gatagtttac atgataagcg gatttttat 180 ttaacacttt ttcccgtgta tgtcctcgta ggtcaactca tttcattatt attagttgag 240
cacggatgga ttctaatcga acttggaggt attaaaagct atcccattgg ttcaattctt 300
tttatggcgt taacaatagt tttattccat tttatcatat ttttaactgt aaaaatttca 360
atattcaaat ttgatcgaac atgtattgat aagttaagtg gtaattcttt tatttattac 420
ttgccgattt tttatctatg cttagtatat attcctgttt ttatttatgg ctctgcatta 480
tctgtaacaa atggtaatcg agttgtatac aatcaaataa tatcacctgt tttttttatat 540 ttatttcaaa ttaaacaatt tatacttcct gttgcaggat tgtatttgct taaaaataaa 600
aaaatattta ctatatatct gtttgcaatt ttactatgga atatattgat tggagagaag 660
gcaacgggca tttggcagtc attgtatcca atgctgttac cttatgtttt gataaattat 720 gataaaaataa aaacaaaaaa tatattaata gtattaggtt tttgtattgt atttataacc 780
agtagcatag taattaatta tatatttatt gaaaagtcag gtgctacgtt tatatttgat 840
agaatatcaa tgcaaggaca attgtggtgg tattatttta atgagcacgt tttgttagct 900 aagaccccctc atgaattatc tgaagagttc tcgtcagaat atagtgggct tcttaatctg 960
atgtatcatt caatgcctgc ccatcttttc aatagctata tcgagcgcgg tgtagtcttg 1020
acgagtggtt tccccgcaat atttcttttt tactttggac aatactggct ccttcctacg 1080
ttattatcac cttttctttt tggtttagtt gtctattttt tttcaagaag tttatatagc 1140
ggtagtatat tgagtttgct tatatcaagt aaactatttt ttgcttttac tgtttttttt 1200
gcccgtggag atatcgcaac ttttttagat tataaattgc ttatttatct attgattata 1260
ataattttac aatatttgcc aagggttaag gtttaa 1296

<210> SEQ ID NO 6
<211> LENGTH: 130
<212> TYPE: PRT
<213> ORGANISM: Shigella flexneri

<400> SEQUENCE: 6

```
Ser Glu Asn Gly Gly Ser Arg Asn Lys Lys Gly Ala His Pro Ser Gly
1               5                   10                  15

Glu Arg Thr Ile Gly Tyr Lys Gln Leu Phe Lys Ile Pro Tyr Ile Gly
            20                  25                  30

Leu Thr Ala Asn Tyr Arg His Glu Asn Phe Glu Phe Gly Ala Glu Leu
        35                  40                  45

Lys Tyr Ser Gly Trp Val Leu Ser Ser Asp Thr Asp Lys His Tyr Gln
    50                  55                  60

Thr Glu Thr Ile Phe Lys Asp Glu Ile Lys Asn Gln Asn Tyr Cys Ser
65                  70                  75                  80

Val Ala Ala Asn Ile Gly Tyr Tyr Val Thr Pro Ser Ala Lys Phe Tyr
                85                  90                  95

Ile Glu Gly Ser Arg Asn Tyr Ile Ser Asn Lys Lys Gly Asp Thr Ser
            100                 105                 110

Leu Tyr Glu Gln Ser Thr Asn Ile Ser Gly Thr Ile Lys Asn Ser Ala
        115                 120                 125

Ser Ile
    130
```

<210> SEQ ID NO 7
<211> LENGTH: 265
<212> TYPE: PRT
<213> ORGANISM: Shigella flexneri

<400> SEQUENCE: 7

```
Glu Lys Ala Phe Asn Lys Ile Tyr Met Ala Gly Gly Lys Gly Thr Val
1               5                   10                  15

Lys Ile Asn Ala Lys Asp Ala Leu Ser Glu Ser Gly Asn Gly Glu Ile
            20                  25                  30

Tyr Phe Thr Arg Asn Gly Gly Thr Leu Asp Leu Asn Gly Tyr Asp Gln
        35                  40                  45

Ser Phe Gln Lys Ile Ala Ala Thr Asp Ala Gly Thr Thr Val Thr Asn
    50                  55                  60

Ser Asn Val Lys Gln Ser Thr Leu Ser Leu Thr Asn Thr Asp Ala Tyr
65                  70                  75                  80

Met Tyr His Gly Asn Val Ser Gly Asn Ile Ser Ile Asn His Ile Ile
                85                  90                  95

Asn Thr Thr Gln Gln His Asn Asn Asn Ala Asn Leu Ile Phe Asp Gly
            100                 105                 110

Ser Val Asp Ile Lys Asn Asp Ile Ser Val Arg Asn Ala Gln Leu Thr
        115                 120                 125

Leu Gln Gly His Ala Thr Glu His Ala Ile Phe Lys Glu Gly Asn Asn
    130                 135                 140

Asn Cys Pro Ile Pro Phe Leu Cys Gln Lys Asp Tyr Ser Ala Ala Ile
145                 150                 155                 160

Lys Asp Gln Glu Ser Thr Val Asn Lys Arg Tyr Asn Thr Glu Tyr Lys
                165                 170                 175

Ser Asn Asn Gln Ile Ala Ser Phe Ser Gln Pro Asp Trp Glu Ser Arg
            180                 185                 190
```

-continued

```
Lys Phe Asn Phe Arg Lys Leu Asn Leu Glu Asn Ala Thr Leu Ser Ile
        195                 200                 205

Gly Arg Asp Ala Asn Val Lys Gly His Ile Glu Ala Lys Asn Ser Gln
    210                 215                 220

Ile Val Leu Gly Asn Lys Thr Ala Tyr Ile Asp Met Phe Ser Gly Arg
225                 230                 235                 240

Asn Ile Thr Gly Glu Gly Phe Gly Phe Arg Gln Gln Leu Arg Ser Gly
                245                 250                 255

Asp Ser Ala Gly Glu Ser Ser Phe Asn
            260                 265


<210> SEQ ID NO 8
<211> LENGTH: 39
<212> TYPE: DNA
<213> ORGANISM: Artificial Sequence
<220> FEATURE:
<223> OTHER INFORMATION: Forward primer for Shigella flexneri 2a

<400> SEQUENCE: 8

ggctctagaa gttttatact tttaattttt aatttagtt                            39


<210> SEQ ID NO 9
<211> LENGTH: 29
<212> TYPE: DNA
<213> ORGANISM: Artificial Sequence
<220> FEATURE:
<223> OTHER INFORMATION: reverse primer for Shigella flexneri 2a

<400> SEQUENCE: 9

gccgaattca aatagaacgc tgcccaata                                       29


<210> SEQ ID NO 10
<211> LENGTH: 29
<212> TYPE: DNA
<213> ORGANISM: Artificial Sequence
<220> FEATURE:
<223> OTHER INFORMATION: forward primer for Shigella flexneri 6

<400> SEQUENCE: 10

tcattttcta gaaaaattgc aaacggaat                                       29


<210> SEQ ID NO 11
<211> LENGTH: 32
<212> TYPE: DNA
<213> ORGANISM: Artificial Sequence
<220> FEATURE:
<223> OTHER INFORMATION: reverse primer for Shigella flexneri 6

<400> SEQUENCE: 11

aagaaggaat tcctccattt gatttcatga tt                                   32


<210> SEQ ID NO 12
<211> LENGTH: 32
<212> TYPE: DNA
<213> ORGANISM: Artificial Sequence
<220> FEATURE:
<223> OTHER INFORMATION: forward primer for Shigella dysenteriae 2

<400> SEQUENCE: 12

ttttattcta gaggattctt tcctgcccca ta                                   32


<210> SEQ ID NO 13
<211> LENGTH: 32
<212> TYPE: DNA
```

-continued

```
<213> ORGANISM: Artificial Sequence
<220> FEATURE:
<223> OTHER INFORMATION: reverse primer for Shigella dysenteriae 2

<400> SEQUENCE: 13

aattttgaat tcacatcaac tttcatgcca ca                              32


<210> SEQ ID NO 14
<211> LENGTH: 30
<212> TYPE: DNA
<213> ORGANISM: Artificial Sequence
<220> FEATURE:
<223> OTHER INFORMATION: forward primer for Shigella sonnei 482-79
      (pWR105)

<400> SEQUENCE: 14

gattctagac gttgaggttt cacgtttctc                                  30


<210> SEQ ID NO 15
<211> LENGTH: 29
<212> TYPE: DNA
<213> ORGANISM: Artificial Sequence
<220> FEATURE:
<223> OTHER INFORMATION: reverse primer for Shigella sonnei 482-79
      (pWR105)

<400> SEQUENCE: 15

aacgaattcc gaagacagca ttcgttcaa                                   29


<210> SEQ ID NO 16
<211> LENGTH: 29
<212> TYPE: DNA
<213> ORGANISM: Artificial Sequence
<220> FEATURE:
<223> OTHER INFORMATION: forward primer for Shigella boydii 7

<400> SEQUENCE: 16

ggctctagat cccattggtt caattcttt                                   29


<210> SEQ ID NO 17
<211> LENGTH: 30
<212> TYPE: DNA
<213> ORGANISM: Artificial Sequence
<220> FEATURE:
<223> OTHER INFORMATION: reverse primer for Shigella boydii 7

<400> SEQUENCE: 17

ccggaattct tagctaacaa aacgtgctca                                  30
```

VACCINE COMPOSITION FOR TREATING OR PREVENTING SHIGELLOSIS

CROSS-REFERENCE TO RELATED APPLICATIONS

The present application is a U.S. National Phase of International Application No. PCT/KR2016/004264 filed on Apr. 22, 2016 which claims the benefit of U.S. Provisional Application No. 62/152,221, filed on Apr. 24, 2015, the disclosures of which are incorporated herein by reference in their entirety for all purposes.

TECHNICAL FIELD

The present invention relates to a vaccine composition for treating or preventing shigellosis, and more particularly, to a *Shigella* strain capable of being effectively used in a vaccine composition for preventing shigellosis derived from various *Shigella* species because the surface exposure of a protective antigen existing on a cellular membrane increases due to the destruction of a wzy gene of *Shigella* species, and a vaccine composition for treating or preventing shigellosis including the same.

BACKGROUND ART

*Shigella* sp. is a Gram-negative bacterial pathogen that causes shigellosis in humans by infecting epithelial cells of the colon. *Shigella* primarily infects intestinal epithelial cells, expresses several proteins which provide a mechanism for delivering effectors inducing the bacterial uptake into host cells via phagocytosis. To accomplish the injection of the effectors, *Shigella* uses a type III secretion (TTS) system to induce the entry into epithelial cells and trigger apoptosis in infected macrophages.

Bacteria of *Shigella* sp., including *Shigella dysenteriae* (*S. dysenteriae*), *Shigella flexneri* (*S. flexneri*), *Shigella boydii* (*S. boydii*), and *Shigella sonnei* (*S. sonnei*), are responsible for shigellosis in humans, a disease characterized by the destruction of the colonic epithelium that is responsible for 1 million deaths per year in developing countries. *Shigella dysenteriae* has 15 serotypes, *Shigella flexneri* has 14 serotypes and subtypes, *Shigella boydii* has 20 serotypes, and *Shigella sonnei* has one serotype, but the prevalence of these strains is not evenly distributed.

Although it is possible to control and treat shigellosis outbreaks with antibiotics, the high cost of antibiotics and the constant emergence of antibiotic-resistant *Shigella* species, even against to the newest antibiotics, underscore a need for effective vaccines to help control *Shigella* and related enteroinvasive *E. coli* diseases in the developing regions of the world.

Natural *Shigella* infections confer immunity and provide protection against subsequent infections with homologous virulent *Shigella*. Epidemiologic and volunteer studies have revealed that protective immunity against *Shigella* is directed against the LPS or O-specific antigens, and thus is associated with serotypes of *Shigella*. Many studies have been conducted for *Shigella* vaccines including the use of live attenuated *Shigella*, dead *Shigella* whole bacteria, and *Shigella* lipopolyssacharides (LPSs) or O-polysaccharides conjugated to carriers such as proteosomes, tetanus toxoids, and ribosomes. Despite several years of extensive research, however, any effective and inexpensive vaccines against such *Shigella* species are not yet available.

When the attenuated *Shigella* strains are used as live oral vaccines, it has been demonstrated to induce protective efficacy. The results of clinical trials of genetically well characterized invasive *Shigella* vaccines are promising. It has been demonstrated orally administered CVD1208, SC602, WRSS1, and WRSd1 vaccines are safe and immunogenic in volunteer trials, and particularly that SC602 protects against shigellosis. Clinical trials using CVD1208 demonstrated that the symptoms of mild fever and diarrhea, which are observed when using some of the live *Shigella* vaccines, may be reduced by elimination of sen and set genes from the vaccine strains. Studies on *Shigella* diarrhea in six Asian countries indicated that a relative distribution of *Shigella* species isolated from patients varies for different countries and sites. Moreover, the *Shigella flexneri* serotypes are highly heterogeneous in a distribution thereof from site to site, and even from year to year. The heterogeneous distribution of *Shigella* species and serotypes suggest that multivalent or cross-protective *Shigella* vaccines will be required to prevent shigellosis all over the world. Vaccines that aim to confer a wide spectrum of coverage may need to include all important *Shigella* serotypes. To solve such a dilemma, a vaccine strategy based on the use of 'pentavalent formulations' including the attenuated *Shigella sonnei* and *Shigella dysenteriae* 1 strains along with *Shigella flexneri* 2a, 3a and 6 strains has been advocated. On the other hand, the use of complex structures consisting of *Shigella*-derived serotype-specific and cross-reactive antigens such as whole dead or live attenuated bacteria has, for example, been considered to be a promising approach to vaccinate against infections caused by the most common species and serotypes of *Shigella* (WO 2010/046778 A2).

Meanwhile, thick O-polysaccharides exist on a cell wall due to an action of a wzy enzyme (O-antigen polymerase) in the case of the *Shigella* species, and thus various protein antigens existing on a cellular membrane and common or specific to the species are buried in a cell wall to block exposure to immune cells. Therefore, such protein antigens have many limitations in use for immunity against *Shigella*.

DISCLOSURE

Technical Problem

Therefore, it is an aspect of the present invention to provide a genetically engineered *Shigella* strain in which surface exposure of a cross-protective antigen increases, and a vaccine composition for treating or preventing shigellosis using the *Shigella* strain.

Technical Solution

To solve the above problems, the present invention provides a *Shigella* strain in which surface exposure of a protective antigen existing on a cellular membrane increases due to the destruction of a wzy gene of *Shigella* species.

According to one exemplary embodiment of the present invention, the wzy gene may have one base sequence selected from the group consisting of SEQ ID NOs: 1 to 5, but the present invention is not limited thereto.

According to another exemplary embodiment of the present invention, the protective antigen may be an IcsP2 or SigA2 protein, but the present invention is not limited thereto. According to preferred exemplary embodiments of the present invention, the IcsP2 protein may have an amino acid sequence set forth in SEQ ID NO: 6, and the SigA2 protein may have an amino acid sequence set forth in SEQ ID NO: 7, but the present invention is not limited thereto.

According to one exemplary embodiment of the present invention, the *Shigella* sp. may be selected from the group consisting of *Shigella dysenteriae, Shigella flexneri, Shigella boydii*, and *Shigella sonnei*. According to preferred exemplary embodiments of the present invention, the *Shigella* sp. may be selected from the group consisting of *Shigella dysenteriae* type 1, *Shigella dysenteriae* 2, *Shigella flexneri* 2a, *Shigella flexneri* 3a, *Shigella flexneri* 5a, *Shigella flexneri* 5b, *Shigella flexneri* 6, *Shigella boydii* serotype 4, *Shigella boydii* 7, and *Shigella sonnei* 482-79, but the present invention is not limited thereto.

Also, the present invention provides a vaccine composition for treating or preventing shigellosis, which includes the aforementioned *Shigella* strain in which surface exposure of a protective antigen existing on a cellular membrane increases due to the destruction of a wzy gene of *Shigella* sp.

According to one exemplary embodiment of the present invention, the *Shigella* strain may be an attenuated strain that may be selected from the group consisting of a live strain and a dead strain.

According to another exemplary embodiment of the present invention, the vaccine composition may further include an adjuvant, and the adjuvant may be selected from the group consisting of an aluminum salt, an immune stimulating complex (ISCOM), a saponin-based adjuvant, an oil-in-water emulsion, a water-in-oil emulsion, a toll-like receptor ligand such as a muramyl dipeptide, *E. coli* LPS, an oligonucleotide containing unmethylated DNA, poly(I:C), lipoteichoic acid, a peptidoglycan, a cholera toxin, a heat-labile *E. coli* enterotoxin, a pertussis toxin, and a Shiga toxin, but the present invention is not limited thereto.

According to one exemplary embodiment of the present invention, the vaccine composition may be administered by injection or via a mucosal route, but the present invention is not limited thereto. According to preferred exemplary embodiments of the present invention, the vaccine composition may be administered by subcutaneous, intradermal, or intramuscular injection, and the mucosal route may be selected from the group consisting of oral, buccal, sublingual, intranasal, and rectal, but the present invention is not limited thereto.

According to one exemplary embodiment of the present invention, an effective dose of the vaccine composition may be in a range of approximately 10 μg to approximately 2 mg, but the present invention is not limited thereto.

Advantageous Effects

The *Shigella* strain of the present invention has a cell wall with a reduced thickness because a gene encoding a protein required for polymerization of an O-saccharide antigen is deleted. Therefore because membrane antigens including protein antigens commonly existing in different *Shigella* species are more exposed to immune cells, the *Shigella* strain can be effectively used as a vaccine composition for treating or preventing shigellosis derived from various *Shigella* sp.

*Shigella* and ΔWZY strains are analyzed by 14% tris/tricine SDS PAGE (30 ng/lane; 16.5% gel and 100 ng/lane in the case of *Shigella flexneri* 2a WT and ΔWZY) and silver staining. A ladder pattern specific to the LPS (O-antigen polymerization) is observed from the wild type, but such a pattern disappears from the ΔWZY.

Figure 3A:
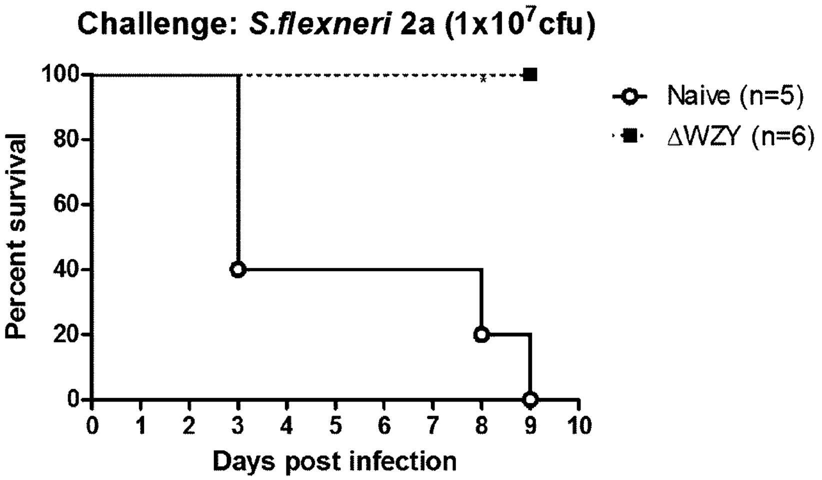
Figure 3B:
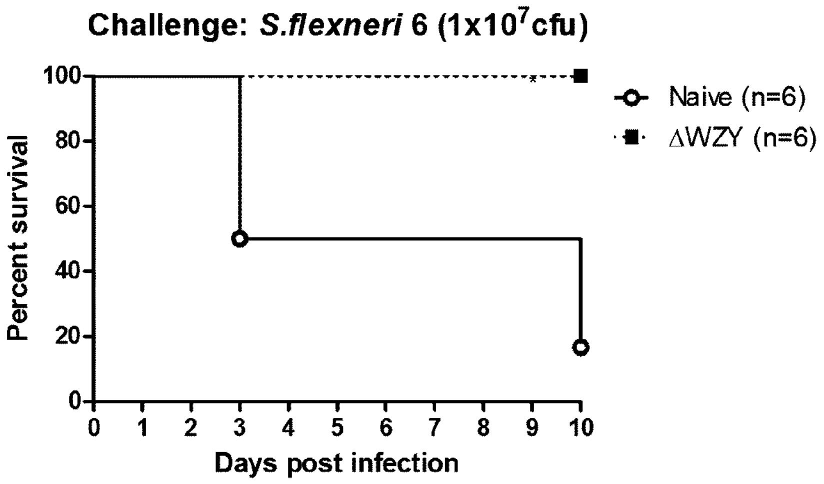
Figure 3C:
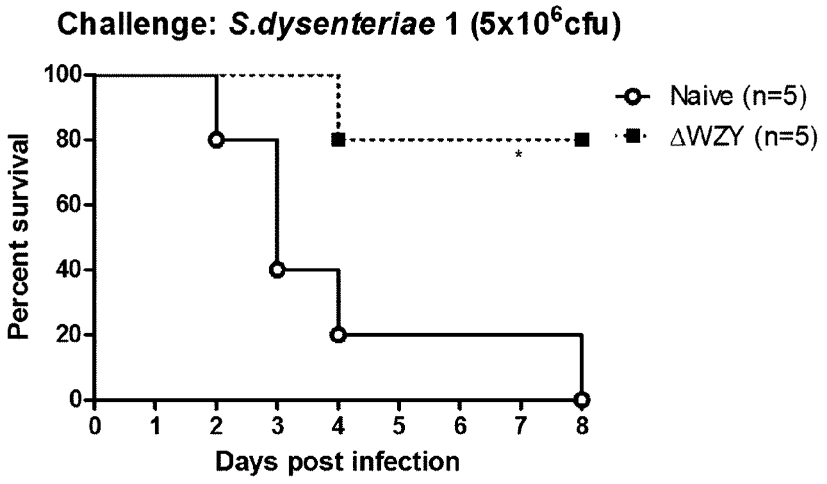

FIGS. 3A to 3C are graphs illustrating survival rates of laboratory animals after challenges. Mice are intranasally immunized with ΔWZY three times at intervals of 2 weeks. One week after the last immunization, the mice are intranasally challenged with *Shigella flexneri* 2a or 6 and *Shigella dysenteriae* 1. The survival of the animals is monitored daily. * represents a value of $p<0.05$ using a log-rank test.

Figure 4A:
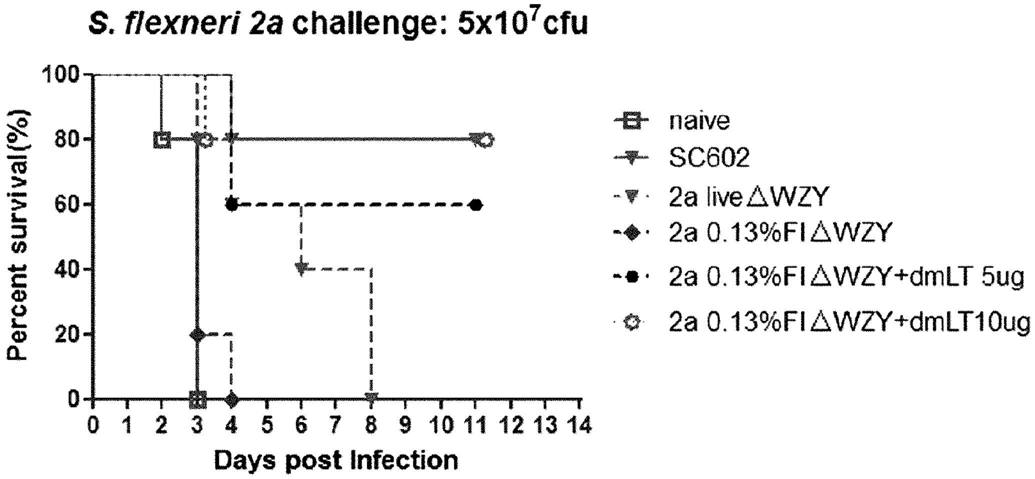
Figure 4B:
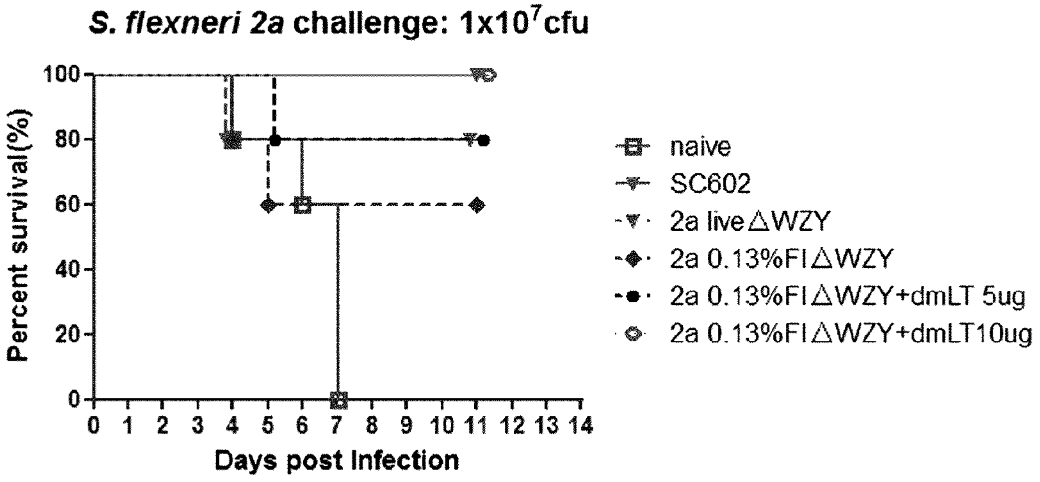
Figure 4C:
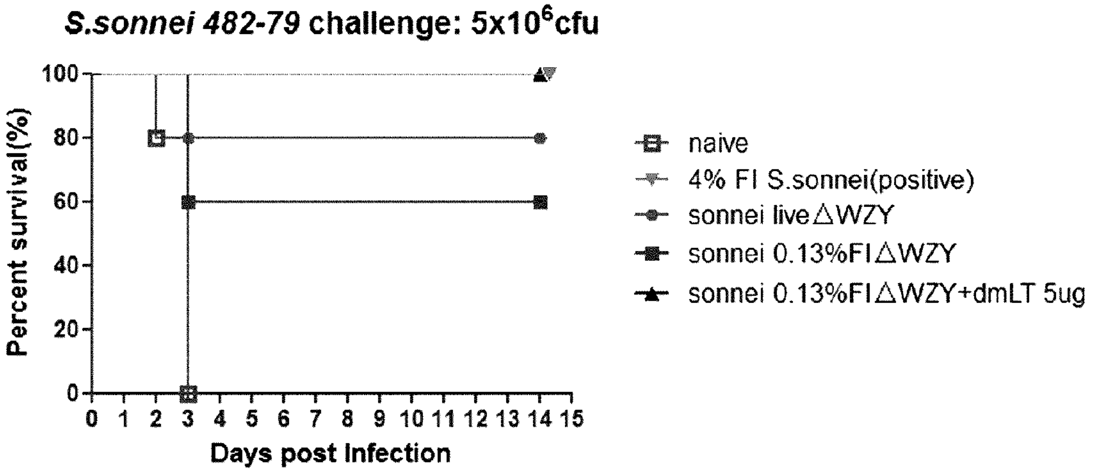

FIGS. 4A to 4C are graphs illustrating that ΔWZY provides protection against homologous challenges of *Shigella* in mice. Mice are intranasally immunized with live ΔWZY, formalin-inactivated ΔWZY (FI ΔWZY), or each of positive strains (*Shigella flexneri* 2a-SC602; and *Shigella sonnei*-4% FI wild type) three times at intervals of 2 weeks. One week after the last immunization, the mice are intranasally challenged with *Shigella flexneri* 2a 2457T, and *Shigella sonnei*. The survival of the animals is monitored daily. Five to six mice are used per each group (N=5 to 6).

Figure 5A:
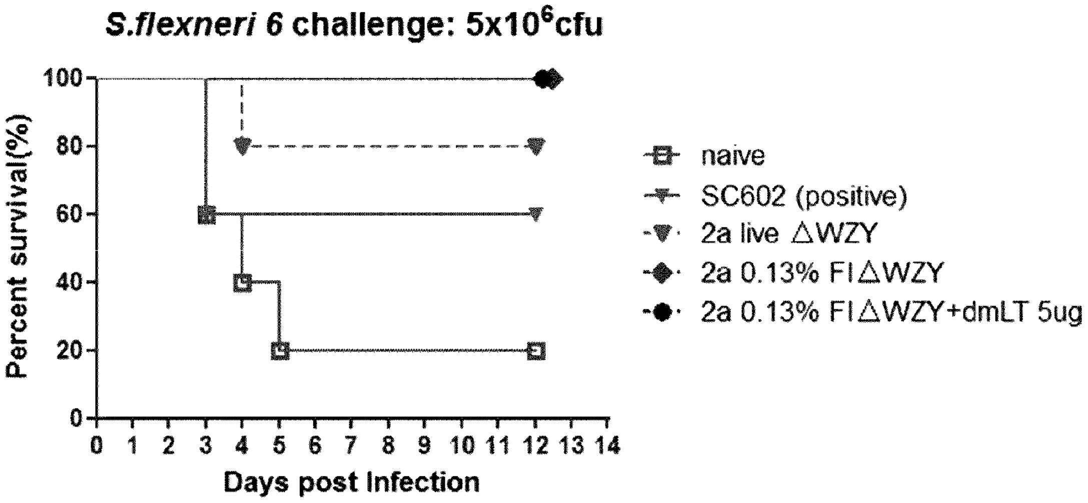
Figure 5B:
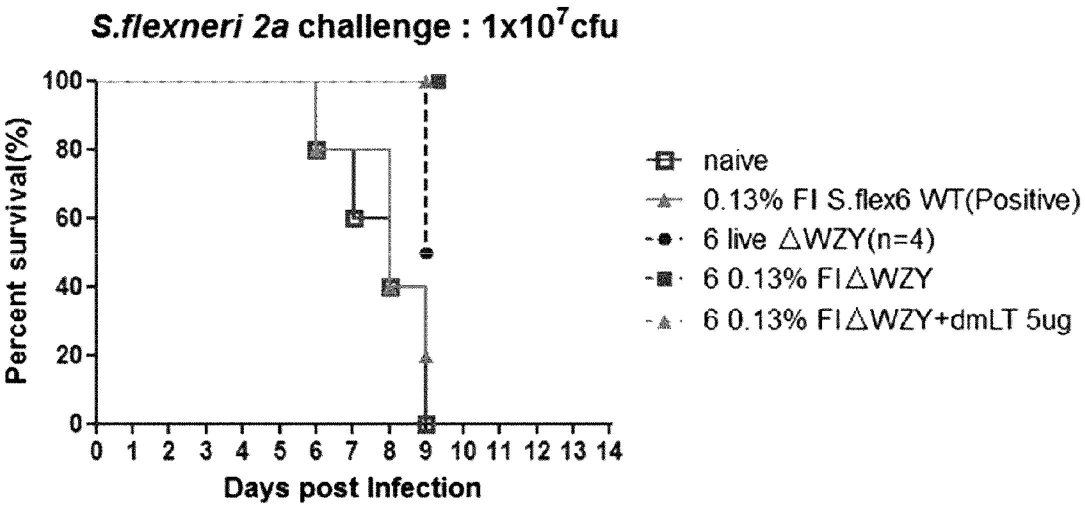

FIGS. 5A and 5B are graphs illustrating results of survival tests for heterologous protection. Mice are intranasally immunized with live ΔWZY, formalin-inactivated ΔWZY (FI ΔWZY), or each of positive strains (*Shigella flexneri* 2a-SC602; *Shigella flexneri* 6-0.13% FI wild type) three times at intervals of 2 weeks. One week after the last immunization, the mice are intranasally challenged with *Shigella flexneri* 2a 2457T or 6. The survival of the animals is monitored daily. Five mice are used per each group (N=5).

Figure 6A:
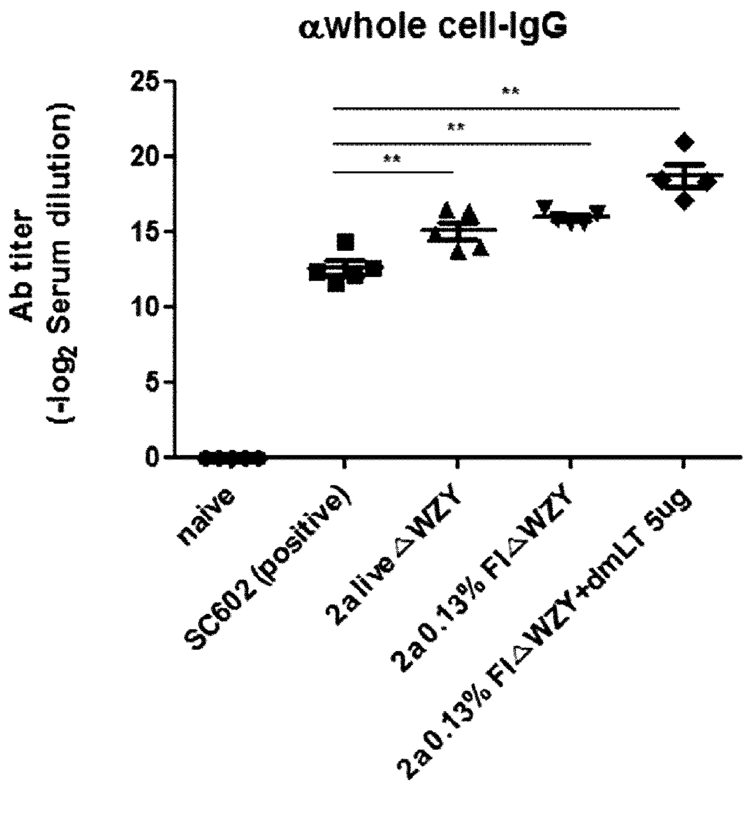
Figure 6B:
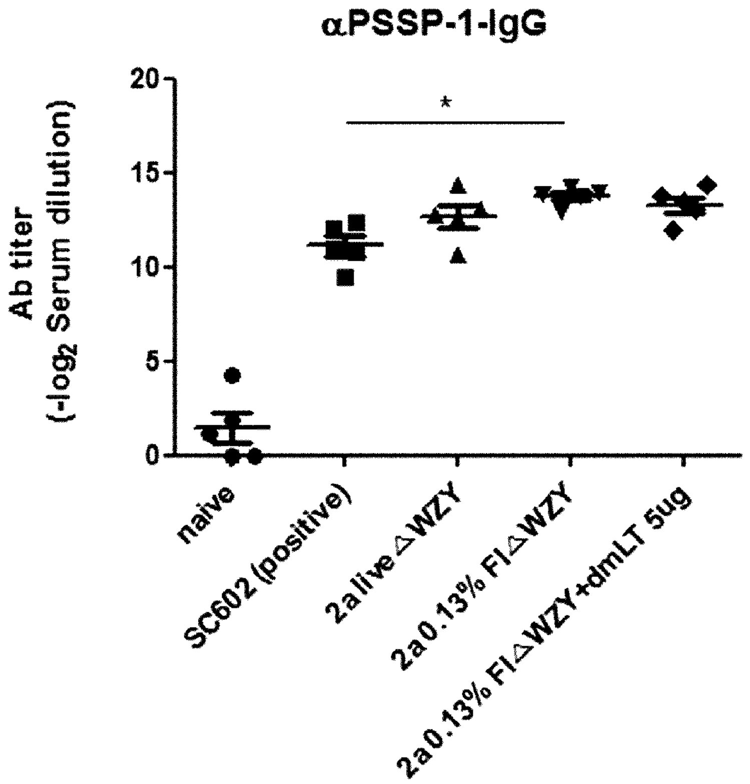
Figure 7A:
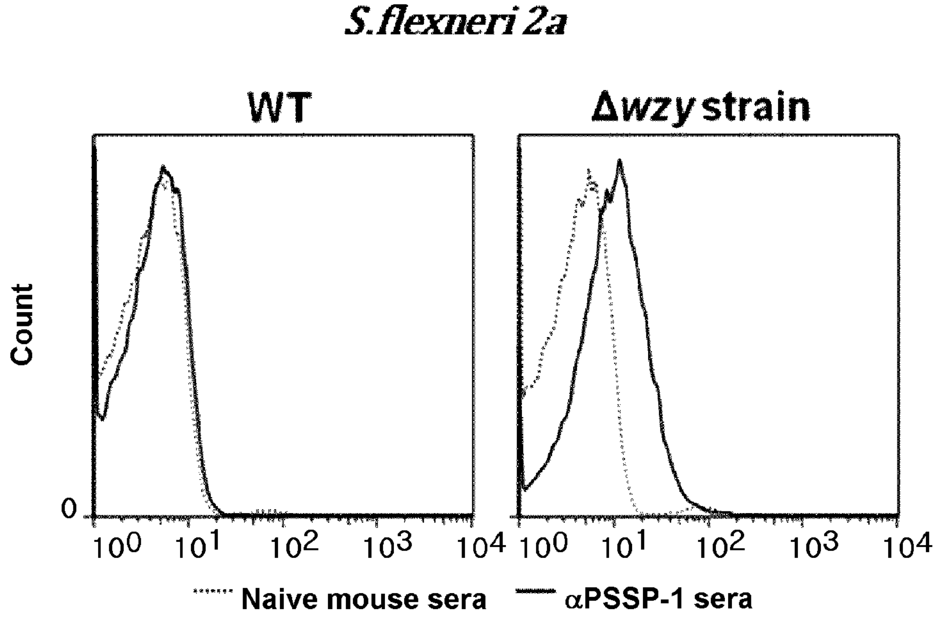
Figure 7B:
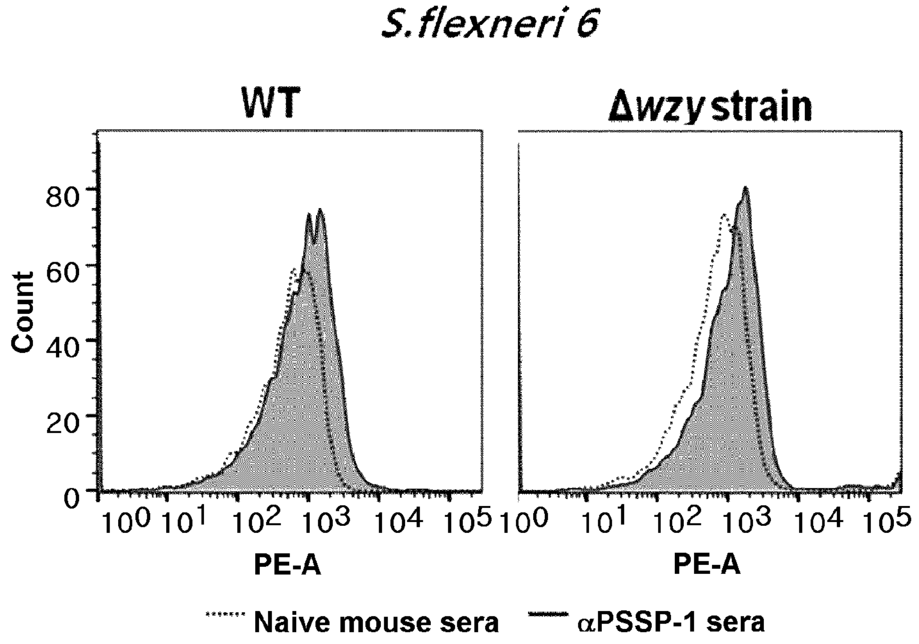
Figure 7C:
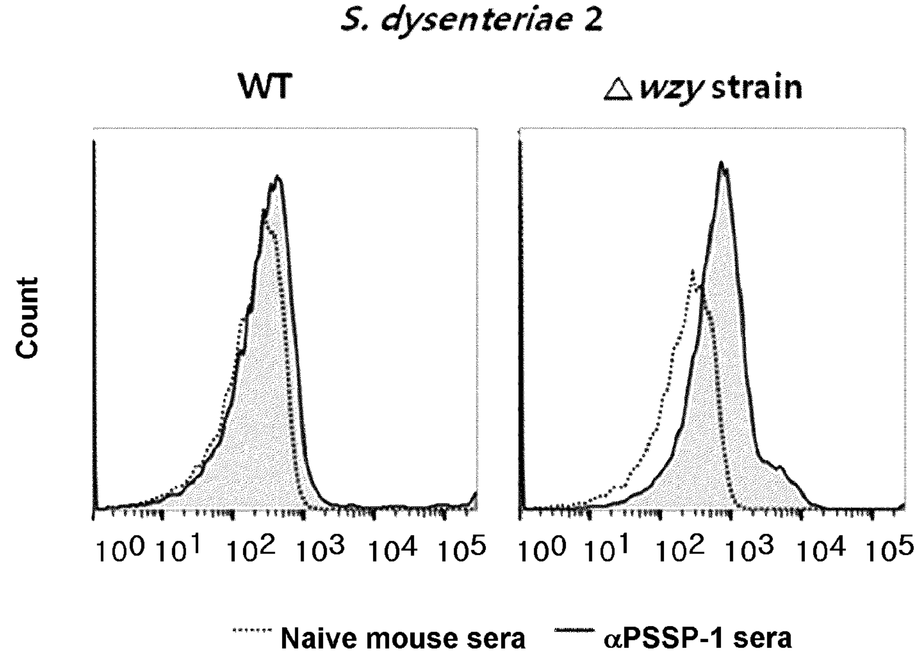
Figure 7D:
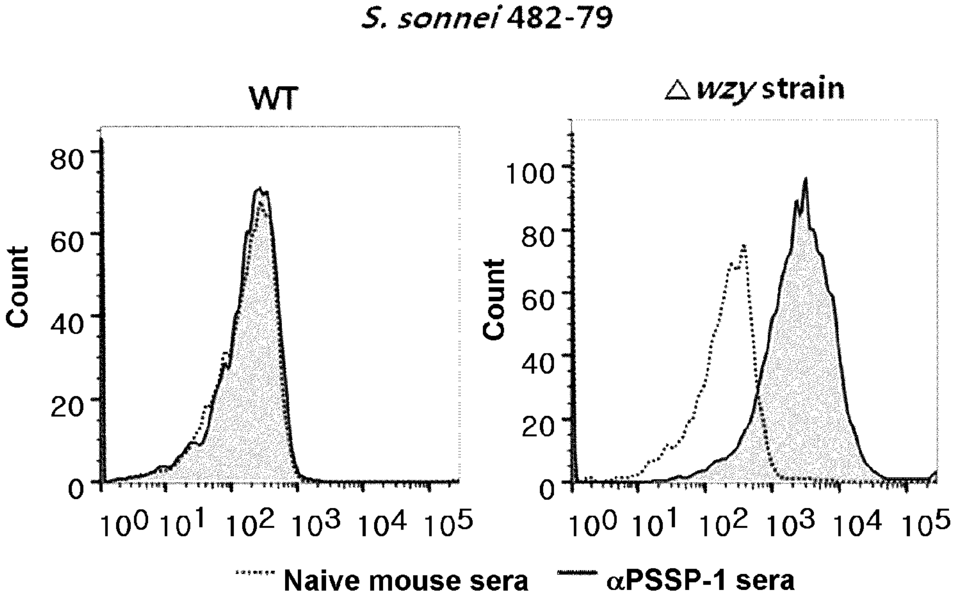
Figure 7E:
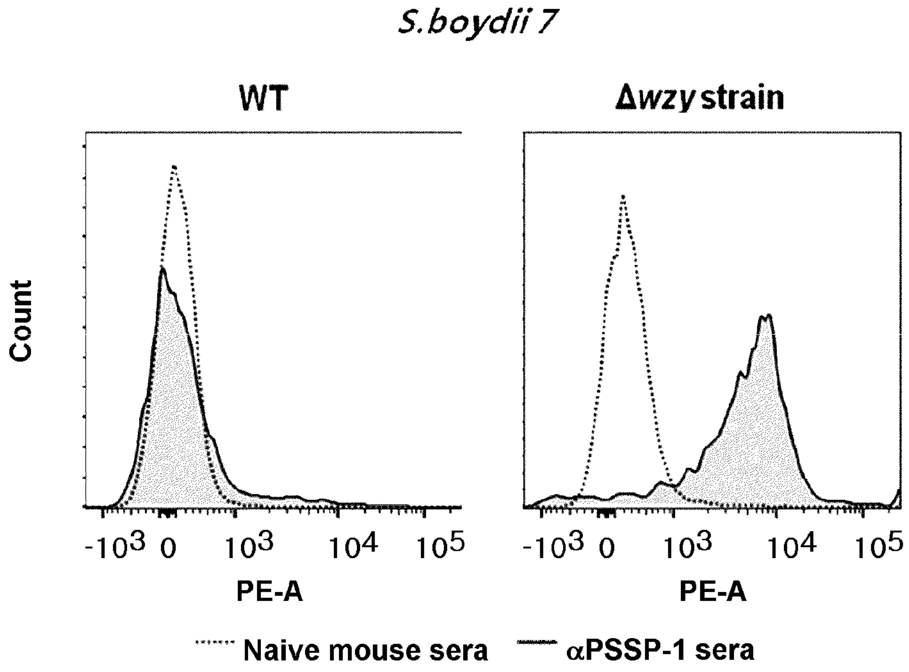

FIGS. 6A and 6B are graph illustrating that ΔWZY immunization in mice induces systemic humoral and local immune responses. Mice are intranasally immunized with 5 μg of each of live SC602, live *Shigella flexneri* 2a (ΔWZY), *Shigella flexneri* 2a (0.13% FIΔWZY), and *Shigella flexneri* 2a (0.13% FIΔWZY+dmLT) 3 times at intervals of 2 weeks. Six days after the third immunization, a serum is collected from the individual mice and IgG is detected by ELISA. * represents a value of $p<0.05$ using a t-test (n=4 to 5).

FIGS. 7A to 7E are graph illustrating results of flow cytometric analysis of expression of pan-*Shigella* surface protein, PSSP on bacteria (using an anti-PSSP-1 (=IcsP2) antibody). A larger amount of IcsP is detected in ΔWZY, compared to wild-type *Shigella*. It is assumed that an outer membrane protein, IcsP, is buried by O-polysaccharides in the wild-type strain but easily detected on a surface of the ΔWZY due to a shorter length of one unit O-antigen.

BEST MODE

The present invention provides a *Shigella* strain in which surface exposure of a protective antigen existing on a cellular membrane increases due to the destruction of a wzy gene of *Shigella* species, and a vaccine composition for treating or preventing shigellosis, which includes the *Shigella* strain.

Figure 1:
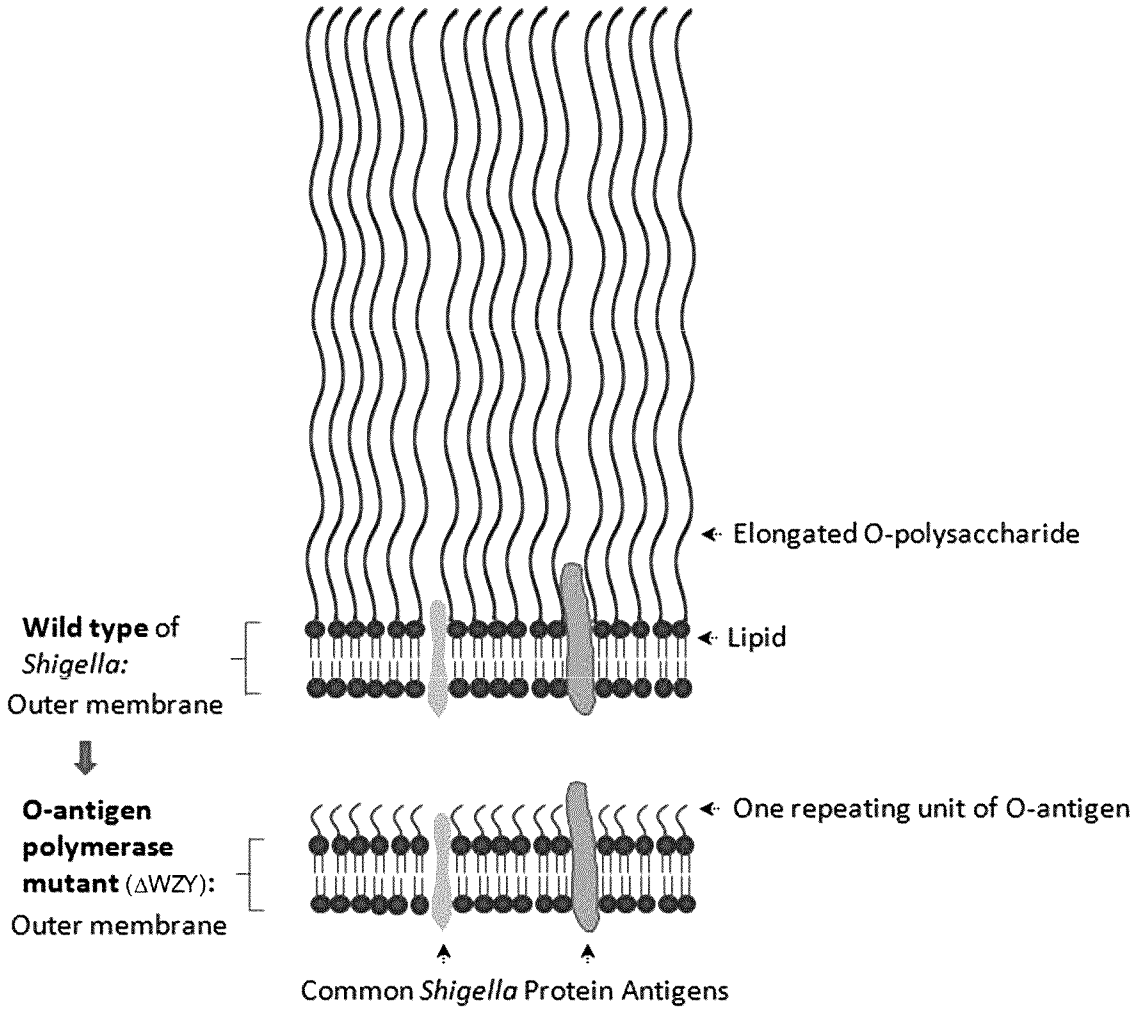
FIG. 1 is a diagram schematically showing a cell wall structure of a wild-type *Shigella* strain and a ΔWZY *Shigella* strain according to the present invention.

According to one exemplary embodiment of the present invention, an attenuated *Shigella* strain (hereinafter referred to as 'ΔWZY') is prepared by destructing a wzy (O-antigen polymerase) gene. According to preferred exemplary embodiments of the present invention, an attenuated *Shigella flexneri* (*S. flexneri*) 2a strain is prepared by destructing a wzy (O-antigen polymerase) gene, and the resulting *Shigella flexneri* 2a ΔWZY expresses only one unit O-antigen, and thus has a cell wall with a remarkably reduced thickness, compared to the wild-type strain (see FIG. 1). According to another exemplary embodiment of the present invention, the ΔWZY strain shows increased exposure of surface protein antigens, compared to the native strain.

According to preferred exemplary embodiments of the present invention, the *Shigella* strain of the present invention has polysaccharides on a cell wall with a reduced thickness, and thus shows an increased surface exposure of potentially protective antigens which are buried in the cell wall of the wild-type strain. Therefore, an immunization strategy using the mutant strain whose cell wall has a reduced thickness due to the destruction of the wzy gene as described above may be effectively applied to immunization with other gram-negative bacteria as well as the *Shigella* sp.

According to one exemplary embodiment of the present invention, when the *Shigella flexneri* 2a ΔWZY is intranasally administered to mice, the mice are protected against experimental lung pneumonia induced by strains belonging to different species and serotypes, including *Shigella flexneri* 2a, *Shigella flexneri* 6, and *Shigella dysenteriae* (*S. dysenteriae*) 1.

According to one exemplary embodiment of the present invention, other ΔWZY strains of *Shigella* species such as *Shigella sonnei* 482-79 (pWR105), *Shigella dysenteriae* 2, and *Shigella flexneri* 6 ΔWZY are prepared, and animal experiments are planned for cross-protection against *Shigella* challenges, followed by ΔWZY immunization with or without an adjuvant (dmLT) (E. B. Norton, L. B. Lawson, L. C. Freytag, J. D. Clements, Characterization of a mutant *Escherichia coli* heat-labile toxin, LT (R192G/L211A), as a safe and effective oral adjuvant, Clin Vaccine Immunol 18 (2011) 546-551).

According to preferred exemplary embodiments of the present invention, preventive vaccination with the genetically modified *Shigella* strain of the present invention with an enhanced exposure of common outer membrane proteins may be used alone or in combination with adjuvant as one component of a *Shigella* vaccine formulation.

According to one exemplary embodiment of the present invention, the *Shigella* strain disclosed in the present invention may be administered together with a pharmaceutically acceptable diluent. Such a formulation may be administered by injection (subcutaneous, intradermal, or intramuscular), or may be locally applied onto the skin using an adhesive patch. On the other hand, the vaccine may be administered via a mucosal route (oral, buccal, sublingual, intranasal, nasal drops, rectal) using a pharmaceutically acceptable vehicle. The *Shigella* strain may also be mixed with an adjuvant to improve the ensuing immune responses. Examples of such an adjuvant may include an aluminum salt, ISCOM, a saponin-based adjuvant, oil-in-water and water-in-oil emulsions, a toll-like receptor ligand such as a muramyl dipeptide, *E. coli* LPS, an oligonucleotide containing unmethylated DNA, poly(I:C), lipoteichoic acid, and a peptidoglycan, but the present invention is not limited thereto. Active derivatives such as a cholera toxin, a heat-labile *E. coli* enterotoxin, a pertussis toxin, a Shiga toxin, and an analogue may be used as the enterotoxin and adjuvant thereof.

According to the present invention, various means and techniques, including what are generally used in molecular immunology, cellular immunology, pharmacology and microbiology, may fall within the technical sprits and scopes of the present invention. Such means and techniques are specifically disclosed in various prior-art documents known to a person having ordinary skill in the art. The abbreviations disclosed in this specification correspond to units of measure, techniques, properties, or compounds as follows: "min" represents minute, "h" represents hour(s), "μL" represents microliter(s), "mL" represents milliliter(s), "mM" represents millimole, "M" represents mole, "mmole" represents millimole(s), "kb" represents kilobase, "bp" represents a base pair(s), and "IU" represents an international unit.

The term "polymerase chain reaction" is abbreviated as PCR; the term "reverse transcriptase polymerase chain reaction" is abbreviated as RT-PCR; the term "untranslated region" is abbreviated as UTR; the term "sodium dodecyl sulfate" is abbreviated as SDS; and the term "high-pressure liquid chromatography" is abbreviated as HPLC.

The term "amplification" of DNA as used in the present invention denotes the use of a polymerase chain reaction (PCR) to increase a concentration of a certain DNA sequence in a mixture of DNA sequences.

The term "polynucleotide", "nucleotide sequence" or "base sequence" is a series of nucleotide bases (also referred to as "nucleotides") in a nucleic acid such as DNA and RNA, and represents any chain of two or more nucleotides. A nucleotide sequence typically carries genetic information, including the information used by cellular machinery to produce proteins and enzymes. The terms include double- or single-stranded genomic and cDNA, RNA, any synthetic and genetically manipulated polynucleotides, and both sense and anti-sense polynucleotides (although only sense stands are being represented in the present invention). This includes single- and double-stranded molecules, i.e., DNA-DNA, DNA-RNA, and RNA-RNA hybrids, as well as "protein nucleic acids" (PNAs) formed by conjugating bases to an amino acid backbone. This also includes nucleic acids containing modified bases, for example thio-uracil, thio-guanine, and fluoro-uracil.

In the present invention, the nucleic acids may be flanked by natural regulatory (expression control) sequences, or may be associated with heterologous sequences including promoters, internal ribosome entry sites (IRES) and other ribosome-binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "capping", substitution of one or more naturally occurring nucleotides with an analogue, and internucleotide modifications such as, for example, modifications with uncharged linkages (e.g., methyl phosphonate, phosphotriester, phosphoroamidate, carbamate, etc.) and modifications with charged linkages (e.g., phosphorothioate, phosphorodithioate, etc.). Polynucleotides may, for example, contain one or more additional covalently linked moieties such as proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by forming a methyl or ethyl phosphotriester or an alkyl phosphoramidate linkage. In the present invention, the polynucleotides may also be modified with a label capable of providing a detectable signal either directly or indirectly. Exemplary labels include radioisotopes, fluorescent molecules, biotins, and the like.

The term "nucleic acid hybridization" refers to anti-parallel hydrogen bonding between two single-stranded nucleic acids, in which A pairs with T (or U in the case of an RNA nucleic acid) and C pairs with G. Nucleic acid molecules are "hybridizable" to each other when at least one strand of one nucleic acid molecule may form hydrogen bonds with complementary bases of another nucleic acid molecule under given stringency conditions. The stringency of hybridization is determined, for example, by (i) a temperature at which hybridization and/or washing is performed, and (ii) an ionic strength, and (iii) a concentration of a denaturant such as formamide in hybridization and washing solutions, as well as other parameters. The hybridization requires that the two strands contain substantially complementary sequences. However, some degree of mismatches may be tolerated depending on the stringency of hybridization. Under "low stringency" conditions, a higher percentage of mismatches are tolerable (i.e., will not prevent formation of an anti-parallel hybrid).

Typically, hybridization of two strands with high stringency requires that the two strands have sequences exhibiting a high degree of complementarity over extended portions of lengths thereof. Examples of high stringency conditions include: hybridization to filter-bound DNA in 0.5 M $NaHPO_4$, 7% SDS, and 1 mM EDTA at 65° C., followed by washing in 0.1×SSC/0.1% SDS at 68° C. (where 1×SSC includes 0.15 M NaCl and 0.15 M sodium citrate) or washing for oligonucleotide molecules in 6×SSC/0.5% sodium pyrophosphate at approximately 37° C. (in the case of approximately 14 nucleotide-long oligos), at approximately 48° C. (in the case of approximately 17 nucleotide-long oligos), at approximately 55° C. (in the case of 20 nucleotide-long oligos), and at approximately 60° C. (in the case of 23 nucleotide-long oligos). Therefore, the term "high-stringency hybridization" refers to a combination of a solvent and a temperature in which two strands will pair to form a "hybrid" helix only when the two strands have almost perfectly complementary nucleotide sequences.

Intermediate or moderate stringency conditions (for example, an aqueous solution of 2×SSC at 65° C.; optionally, for example, hybridization to filter-bound DNA in 0.5 M $NaHPO_4$, 7% SDS, and 1 mM EDTA at 65° C., followed by washing in 0.2×SSC/0.1% SDS at 42° C.), and low stringency conditions (for example, an aqueous solution of 2×SSC at 55° C.) require that two strands have the corresponding less overall complementarity necessary for hybridization to occur between two sequences thereof. Certain temperature and salt conditions for any given stringency hybridization reaction depend on a concentration of target DNA and a length and base compositions of a probe, and are generally determined empirically in conventional preliminary experiments.

As used in the present invention, the term "standard hybridization conditions" refers to a hybridization condition that allows hybridization of sequences having at least 75% sequence identity. According to specific exemplary embodiments, hybridization conditions with higher stringency may be used to allow hybridization of only sequences having at least 80% sequence identity, at least 90% sequence identity, at least 95% sequence identity, or at least 99% sequence identity.

A nucleic acid molecule that "hybridizes" to any desired nucleic acids of the present invention may have any length. In one exemplary embodiment, such nucleic acid molecule has a length of at least 10, at least 15, at least 20, at least 30, at least 40, at least 50, and at least 70 nucleotides. In another exemplary embodiment, a nucleic acid molecule to be hybridized has substantially the same length as certain desired nucleic acids.

The term "isolated" means that a target material is removed from environments in which the target material is normally found. Therefore, an isolated biological material may be free of cellular components, i.e., components of the cells in which the biological material is found or produced. For example, isolated nucleic acid molecules include PCR products, isolated mRNA, cDNA, or restriction fragments. For example, the isolated nucleic acid molecules also include sequences inserted into plasmids, cosmids, artificial chromosomes, and the like. The isolated nucleic acid molecules are preferably excised from the genome in which the nucleic acid molecules may be found. More preferably, the isolated nucleic acid molecules are no longer joined to non-regulatory sequences, non-coding sequences, or to other genes located upstream or downstream of the nucleic acid molecules when found in the genome. An isolated protein may be associated with other proteins or nucleic acids, or both, with which the isolated protein is associated in the cell, or associated with cellular membranes when the isolated protein is a membrane-associated protein.

The term "host cell" includes individual cells or cell culture broths which may be a recipient for vectors or a recipient for incorporation of polynucleotide molecules, or may have the recipient. In the present invention, a host cell may be a bacterium, a mammalian cell, an insect cell, or a yeast cell.

The term "treating" or "treatment" of a condition, disorder or symptom includes:

(1) preventing or delaying the appearance of clinical or sub-clinical signs of the condition, disorder or symptom from developing in a mammal that may be afflicted with or predisposed to the condition, disorder or symptom but does not yet experience or express clinical or subclinical signs of the condition, disorder or symptom; or (2) inhibiting the condition, disorder or symptom, that is, arresting, reducing or delaying the onset of a disease or a relapse thereof (in case of maintenance therapy) or one of clinical or sub-clinical signs thereof; or (3) relieving a disease, that is, causing regression of the condition, disorder or symptom or one of clinical or sub-clinical signs thereof.

The benefit to a subject to be treated is either statistically significant or at least perceptible to patients or medical physicians.

The "immune response" refers to the development of a cell-mediated and/or antibody-mediated immune response to a composition or vaccine of interest in the host. Such a response is generally carried out on the subject producing antibodies, B cells, helper T cells, and/or cytotoxic T cells specifically directed to an antigen or antigens included in the composition or vaccine of interest. The immune response may also include regulatory T-cells whose activities are beyond those of organisms of interest, and thus may suppress other immune or allergic responses.

The "therapeutically effective amount" refers to an amount of a compound, adjuvant or vaccine composition which, when administered to a mammal for the purpose of treating a condition, disorder or symptom, is sufficient to effect such treatment. The "therapeutically effective amount" will vary depending on the compound, bacteria or analogue to be administered, as well as a disease and severity thereof, and the age, weight, physical condition, and responsiveness of the mammal to be treated.

The "prophylactically effective amount" refers to an amount effective in achieving a desired prophylactic result at a desired dose and for a desired period of time. Typically, because a prophylactic dose is used prior to a disease or at an earlier stage of the disease, the prophylactically effective amount will be less than the therapeutically effective amount.

Although it is possible to use the composition provided in the present invention for the purpose of therapy, the composition may be preferably administered in the form of a pharmaceutical formulation, for example, an admixture with a suitable pharmaceutical excipient, diluent or carrier selected with regard to the intended route of administration and standard pharmaceutical practice. Therefore, according to one aspect of the present invention, there is provided a pharmaceutical composition or formulation including at least one active composition, or a pharmaceutically acceptable derivative thereof, in association with a pharmaceutically acceptable excipient, diluent and/or carrier. The excipient, diluent and/or carrier should be "acceptable" in terms of being compatible with the other ingredients of the formulation and not deleterious to the recipient thereof.

The composition of the invention may be formulated to be administered in any convenient manner for use in drugs for humans or vertebrates. Therefore, the scope of the present invention includes pharmaceutical compositions including a product of the present invention that is adapted for use in drugs for humans or vertebrates.

According to preferred exemplary embodiments, the pharmaceutical composition is conveniently administered as a liquid oral formulation. Although there are no physical limitations in delivery of the formulation, oral delivery is preferred because the oral delivery is easy and convenient and oral formulations readily accommodate an additional mixture such as milk, yoghurt, and infant formula. Other oral formulations are well known in the related art, and include tablets, caplets, gelcaps, capsules, and medical foods. For example, the tablets may be made by a well-known compression technique using a wet, dry or fluidized bed granulation method.

Such oral formulations may be provided for use in a conventional manner with the aid of one or more suitable excipients, diluents, and carriers. Pharmaceutically acceptable excipients assist or make possible formation of a formulation for bioactive materials, and include diluents, binders, lubricants, glidants, disintegrants, coloring agents, and other ingredients. Preservatives, stabilizers, dyes and even flavoring agents may also be provided in the pharmaceutical composition. Examples of the preservatives include sodium benzoate, ascorbic acid, and an ester of p-hydroxybenzoic acid. Antioxidants and suspending agents may be also used. An excipient is pharmaceutically acceptable as long as the excipient is non-toxic and well tolerated upon ingestion, and does not interfere with absorption of bioactive materials, as well as performing a desired function of the excipient.

Acceptable excipients, diluents, and carriers for therapeutic use are well known in the field of pharmaceuticals, and the choice of pharmaceutical excipients, diluents, and carriers may be selected with regard to the intended route of administration and standard pharmaceutical practice.

As used in the present invention, the phrase "pharmaceutically acceptable" refers to a molecular entity and composition that are generally regarded as physiologically tolerable.

The term "patient," "target" or "subject" refers to a mammal and includes human and veterinary targets.

The dosage of an adjuvant formulation or vaccine composition containing the adjuvant will vary widely, depending upon the nature of the disease, the patient's medical history, the frequency of administration, the administration mode, the clearance of the agents from the host, and the like. The initial dose may be larger, followed by smaller maintenance doses. The dose may be administered as infrequently as monthly or annually to maintain an effective immunological memory.

The term "carrier" refers to a diluent, adjuvant, excipient or vehicle with which the compound is administered. Such a pharmaceutical carrier may be a sterile liquid such as water, and oil, including petroleum, animal oil, vegetable oil, or oil of synthetic origin, such as peanut oil, soybean oil, mineral oil, sesame oil, and the like. Water or an aqueous solution, a saline solution, and aqueous dextrose and glycerol solutions are preferably introduced as the carrier, particularly a carrier for injectable solutions. Optionally, the carrier may be a carrier for solid formulations, including one or more selected from a binder (in the case of a compressed pill), a glidant, an encapsulating agent, a flavoring agent, and a coloring agent, but the present invention is not limited thereto.

Also, the present invention encompasses a pharmaceutical composition and a vaccine. The pharmaceutical composition and vaccine composition of the present invention includes a pharmaceutically acceptable carrier or excipient along with the one or more novel *Shigella* antigens and one or more adjuvants. Methods of formulating the pharmaceutical composition and vaccine are well known to those having ordinary skill in the art.

Formulations:

The vaccine compositions of the present invention may include pharmaceutically acceptable diluents, preservatives, solubilizers, emulsifiers, adjuvants and/or carriers. Such compositions have various buffer contents (for example, Tris-HCl, acetate, phosphate), and a pH and ionic strength; and include additives such as surfactants and solubilizers (for example, Tween 80, Polysorbate 80), antioxidants (for example, ascorbic acid, sodium metabisulfite), preservatives (for example, Thimersol, benzyl alcohol), and bulking substances (for example, lactose, mannitol); wherein the materials are incorporated into certain preparations of polymeric compounds such as polylactic acid, polyglycolic acid, and the like or incorporated into liposomes. Hylauronic acid may also be used.

Oral solid formulations are contemplated for use in the present invention. The solid formulations may include tablets, capsules, pills, troches, lozenges, cachets, pellets, powders, or granules. Also, liposomal or proteinoid encapsulation may be used to formulate the compositions of the present invention. Liposomal encapsulation may be used and the liposomes may be derivatized with various polymers. Generally, the formulations will include the therapeutic agents and inert ingredients which allow for protection of the stomach against environments, and release of the biologically active material in the intestine.

Also, liquid formulations for oral administration, which include a pharmaceutically acceptable emulsion, a solution, a suspension, and syrup, are contemplated for use in the present invention. In this case, the liquid formulations may contain other components including inert diluents; an adjuvant, a wetting agent, an emulsifying agent, and a suspending agent; and a sweetening agent, a flavoring agent, a coloring agent, and a perfuming agent.

For oral formulations, the location of release of the components may be the stomach, the small intestine (the duodenum, the jejunem, or the ileum), or the large intestine. A person having ordinary skill in the art may employ formulations, which will not dissolve in the stomach but whose materials will be released into the duodenum or elsewhere in the intestine, through the use of an enteric coating. Examples of the more common inert ingredients that are used as the enteric coating include cellulose acetate trimellitate (CAT), hydroxypropylmethyl cellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. Such coatings may be used as mixed films.

A coating or mixture of coatings may also be used on tablets, which are not intended to protect the stomach. This may include sugar coatings, or coatings which make it easy to swallow the tablets. Capsules may consist of a hard shell (for example, gelatin) for delivery of dry therapeutic agents (i.e., a powder), and a soft gelatin shell may be used when the capsules are in a liquid form. A shell material for cachets may be thick starch or other edible papers. For pills, lozenges, molded tablets or tablet triturates, a moist massing technique may be used. The formulation of materials for capsule administration may also be in the form of a powder, a lightly compressed plug, or even a tablet. The therapeutic agents may be prepared by compression.

A person having ordinary skill in the art may dilute or increase a volume of the therapeutic agent using an inert material. The diluents may include carbohydrates, especially mannitol, β-lactose, anhydrous lactose, cellulose, sucrose, modified dextran, and starch. Certain inorganic salts, which include calcium triphosphate, magnesium carbonate, and sodium chloride, may be also be used as fillers. Some commercially available diluents include Fast-Flo, Emdex, STA-Rx 1500, Emcompress, and Avicell.

In the formulation of the therapeutic agent, disintegrants may be incorporated into solid formulations. Materials used as the disintegrates include starch, commercially available starch-based disintegrants, Explotab, sodium starch glycolate, Amberlite, sodium carboxymethyl cellulose, ultramylopectin, sodium alginate, gelatin, orange peel, acid carboxymethyl cellulose, natural sponge, and bentonite, but the present invention is not limited thereto. In this case, all the materials may be used. The disintegrants may also be insoluble cationic exchange resins. Powdered gums may be used as the disintegrants and binders, and may include powdered gums such as agar, Karaya, or tragacanth. Alginic acid and sodium salts thereof are also useful as the disintegrants. The binders may be taken together with the therapeutic agent to form a hard tablet, and include natural product-derived materials such as acacia, tragacanth, starch, and gelatin. Other binders include methyl cellulose (MC), ethyl cellulose (EC), and carboxymethyl cellulose (CMC). Both polyvinyl pyrrolidone (PVP) and hydroxypropylmethyl cellulose (HPMC) may be used to granulate the peptides (or derivatives) in an alcoholic solution.

An antifrictional agent may be included in the formulation to prevent sticking during a formulation process. A lubricant may be used as a layer between the peptides (or derivatives) and the die wall. In this case, the lubricant may include stearic acid including magnesium and calcium salts thereof, polytetrafluoroethylene (PTFE), liquid paraffin, vegetable oil, and wax, but the present invention is not limited thereto. Soluble lubricants such as sodium lauryl sulfate, magnesium lauryl sulfate, polyethylene glycols having various molecular weights, and Carbowax 4000 and 6000 may also be used as the lubricant.

A glidant that may improve the fluidity of drugs during formulation and may aid in rearranging the drugs during compression may be added. The glidant may include starch, talc, pyrogenic silica, and hydrated silicoaluminate.

To aid in dissolving the therapeutic agent into an aqueous environment, a surfactant might be added as a wetting agent. The surfactant may include anionic detergents such as sodium lauryl sulfate, dioctyl sodium sulfosuccinate, and dioctyl sodium sulfonate. Cationic detergents may be used, and may include benzalkonium chloride or benzethomium chloride. The list of potential nonionic detergents that may be included as the surfactant in the formulation includes Lauromacrogol 400, polyoxyl 40 stearate, polyoxyethylene-hydrogenated castor oil 10, 50 and 60, glycerol monostearate, polysorbate 40, 60, 65 and 80, sucrose fatty acid ester, methyl cellulose, and carboxymethyl cellulose. Such surfactants may be present in the formulation of the proteins or derivatives either alone or in a mixture thereof in different ratios.

Controlled-release oral formulations may be used to put the present invention into practice. The therapeutic agent may be incorporated into an inert matrix which permits diffusion or release of the therapeutic agent through a leaching mechanism like gum. A slowly decomposing matrix may also be included in the formulation. Any enteric coatings also have a delayed-release effect. Other types of the controlled release are realized by a method based on an Oros therapeutic system (Alza Corp.), that is, a method in which the therapeutic agent is enclosed in a semipermeable membrane which allows the entry of water and the release of agents through a single small opening due to an osmotic effect.

Other coatings may be used for the formulation. Such coatings include a variety of sugars which may be applied to coating pans. The therapeutic agent may also be provided in a film-coated tablet, and materials used in this case are divided into two categories. The first category consists of nonenteric materials, and includes methyl cellulose, ethyl cellulose, hydroxyethyl cellulose, methylhydroxyethyl cellulose, hydroxypropyl cellulose, hydroxypropylmethyl cellulose, sodium carboxymethyl cellulose, providone, and polyethylene glycol. The second category consists of enteric materials that are generally esters of phthalic acid. A mixture of materials may be used to provide the optimum film coating. The film coating may be performed in a pan coater or in a fluidized bed, or performed by compression coating.

In one exemplary embodiment, the *Shigella* strain disclosed in the present invention may be administered with a pharmaceutically acceptable diluent. Such formulations may be administered by injection (subcutaneous, intradermal, or intramuscular) or may be topically applied onto the skin using an adhesive patch. On the other hand, the vaccine is administered via a mucosal route (oral, buccal, sublingual, nasal drops, aerosol, or rectal) using a pharmaceutically acceptable vehicle. The *Shigella* strain may also be mixed with an adjuvant to enhance a subsequent immune response. Example of such an adjuvant include an aluminium salt, ISCOM, a saponin-based adjuvant, an oil-in-water emulsion, a water-in-oil emulsion, a toll-like receptor ligand such as a muramyl dipeptide, *E. coli* LPS, an oligonucleotide containing unmethylated DNA, poly(I:C), lipoteichoic acid, and a peptidoglycan, but the present invention is not limited thereto. Enterotoxins and adjuvants thereof include active derivatives such as cholera toxins, heat-labile *E. coli* enterotoxins, pertussis toxins, Shiga toxins, and analogues.

Preparations for parenteral administration according to the present invention include a sterile aqueous or non-aqueous solution, a suspension, or an emulsion. Examples of non-aqueous solvents or vehicles include propylene glycol, polyethylene glycol, vegetable oils, such as olive oil and corn oil, gelatin, and injectable organic esters such as ethyl oleate. Such formulations may also contain an adjuvant, a preservative, a wetting agent, an emulsifier, and a dispersing agent. The pharmaceutical compositions may, for example, be sterilized by filtering the compositions through a bacteria-retaining filter, incorporating a sterilizing agent into the compositions, irradiating the compositions, or heating the compositions. These compositions may also be prepared using sterile water or other sterile injectable media, immediately before use thereof.

Vaccines:

In the case of vaccines, it is often observed that a primary challenge with an antigen alone, in the absence of an adjuvant, fails to elicit a humoral or cellular immune response. Therefore, the vaccines of the invention may contain adjuvants including, but not limited to, cholera toxins, fragments and mutants or derivatives having adjuvant properties, *E. coli* heat-labile enterotoxins, fragments and mutants or derivatives having adjuvant properties, oil-in-water and water-in-oil emulsions, toll-like receptor ligands such as a muramyl dipeptide, *E. coli* LPS, oligonucleotides containing unmethylated DNA, poly(I:C), lipoteichoic acid, peptidoglycans. Enterotoxins and adjuvants thereof include active derivatives such as cholera toxins, heat-labile *E. coli* enterotoxins, pertussis toxins, Shiga toxins, and analogues. Other adjuvants such as complete Freund's adjuvants, incomplete Freund's adjuvants, saponin, mineral gels such as aluminum hydroxide, surface active materials such as lysolecithin, pluronic polyols, polyanions, peptides, oil or hydrocarbon emulsions, keyhole limpet hemocyanin, and potentially useful human adjuvants such as N-acetyl-muramyl-L-threonyl-D-isoglutamine (thr-MDP), N-acetyl-normuramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, Bacille Calmette-Guerin (BCG), and *Corynebacterium parvum* may be used. An adjuvant may serve as a tissue depot that slowly releases the antigens and may also serve as a lymphoid system activator that enhances an immune response in a non-specific manner. When the vaccine is intended for use in human subjects, the adjuvant should be pharmaceutically acceptable.

Administration:

Such pharmaceutical compositions and vaccines may be administered orally (in a solid or liquid phase), parenterally (by intramuscular, intraperitoneal, intravenous (IV), or subcutaneous injection), transdermally (either passively or using ionophoresis or electroporation), transmucosally (nasally, vaginally, rectally, or sublingually), or via an inhalation route of administration, or administered using a bioerodible insert, and may be prepared into formulations suitable for each of the routes of administration.

In one preferred exemplary embodiment, the compositions or vaccines are administered by means of pulmonary delivery. The compositions or vaccines are delivered to the lungs of a mammal during inhalation, and traverses the epithelial lining of the lungs into the blood stream.

According to one exemplary embodiment of the present invention, a wide range of mechanical devices designed for pulmonary delivery of therapeutic products, including, but not limited to, a nebulizer, a metered dose inhaler, and a powdered inhaler, all of which are familiar to those skilled in the art, are contemplated. Any specific examples of commercially available devices suitable for the practice of the present invention include an Ultravent nebulizer (Mallinckrodt Inc., St. Louis, Mo.); an Acorn II nebulizer (Marquest Medical Products, Englewood, Colo.); a Ventolin metered dose inhaler (Glaxo Inc., Research Triangle Park, N.C.); and a Spinhaler powdered inhaler (Fisons Corp., Bedford, Mass.). All such devices require the use of formulations suitable for dispensing the therapeutic agent. Typically, each of the formulations is specific to the type of devices employed, and may involve the use of appropriate propellant materials, in addition to the conventional diluents, adjuvants, surfactants and/or carriers useful in therapy. Also, the use of liposomes, microcapsules or microspheres, inclusion complexes, or other types of carriers is contemplated.

Formulations for use with a metered dose inhaler device may generally include a finely divided powder containing the therapeutic agent suspended in a propellant with the aid of a surfactant. The propellant may include any conventional materials employed for this purpose, for example chlorofluorocarbon, hydrochlorofluorocarbon, hydrofluorocarbon, or hydrocarbons including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be effectively used as the surfactant.

Formulations to be dispensed from a powdered inhaler device will include a finely divided dry powder containing the therapeutic agent, and may also include a bulking agent, such as lactose, sorbitol, sucrose, or mannitol, in an amount which facilitates dispersal of the powder from the device, e.g., 50 to 90% by weight of the formulation. The therapeutic agent should be most advantageously prepared in the form of particles having an average particle size of 10 mm (or microns) or less, most preferably 0.5 to 5 mm, for the most effective delivery to the distal lung.

Nasal delivery or other mucosal delivery of the therapeutic agent is also contemplated. The nasal delivery allows a direct passage of the composition into the blood stream without any necessity for deposition of the product in the lung after the composition is administered to the nose. Formulations for nasal delivery include those with dextran or cyclodextran and saponin as adjuvants.

The compositions or vaccines of the present invention may be administered in conjunction with one or more additional active ingredients, pharmaceutical compositions, or vaccines. The therapeutic agent of the present invention may be administered to an animal, preferably a mammal, most preferably a human.

Dosage:

Following the methodologies well-established in the related art, an effective dose and toxicity of the compounds and compositions, which are easily used in in vitro tests, are determined in preclinical studies using a small animal model (for example, mice or rats) in which the *Shigella* strain or vaccine compositions have been found to be therapeutically or prophylactically effective and in which these drugs may be administered by the same route proposed for the human clinical trials.

Formulations or dosage forms for use in the present invention need not contain a therapeutically or prophylactically effective amount of the components disclosed in the present invention because such therapeutically or prophylactically effective amount may be achieved by administering a plurality of such formulations or dosage forms.

For any vaccine compositions used in the method of the present invention, the therapeutically or prophylactically effective dose may be preferentially estimated from an animal model. A dose-response curve derived from an animal system is then used to determine testing doses for the initial clinical trials in humans. To determine safety for each of the compositions, the dose and frequency of administra tion should meet or surpass the requirements anticipated for use in the clinical trials.

As disclosed in the present invention, the dose of each of the components in the composition of the present invention is determined to ensure that the dose administered continuously or intermittently does not exceed an amount determined after consideration of the results of animal tests and the individual symptom of a patient. Of course, the certain dose varies depending on the dosage procedure, the symptoms of a patient or a target animal, such as age, body weight, sex, sensitivity, feed, dosage period, drugs used in combination, and the severity of a disease. The appropriate dose and dosage time under certain conditions may be determined by the tests based on the aforementioned indices, but may be refined and ultimately decided based on the judgment of the practitioner and the individual patients' circumstances (age, general condition, severity of symptoms, sex, etc.) according to the standard clinical techniques.

The toxicity and therapeutic or prophylactic efficacy of the compositions of the present invention may be determined according to the standard pharmaceutical procedure in laboratory animals, for example, determined by measuring $LD_{50}$ (a lethal dose for 50% of the population) and $ED_{50}$ (a therapeutically effective dose for 50% of the population). The dose ratio between therapeutic and toxic effects is a therapeutic index, which may then be expressed as the ratio $ED_{50}/LD_{50}$. Compositions exhibiting high therapeutic indices are preferred.

The data obtained from animal studies can be used to formulate a range of doses for use in humans. The therapeutically effective doses in humans preferably fall within a range of circulating concentrations that include the $ED_{50}$ with little or no toxicity. The doses may vary within this range depending on the formulations employed and the route of administration used. Ideally, a single dose of each drug should be used daily.

[Mode for Invention]

Hereinafter, the present invention will be described in detail with reference to exemplary embodiments thereof.

However, it should be understood that the following examples are just preferred examples for the purpose of illustration only and are not intended to limit or define the scope of the present invention.

Example 1: Construction of Knock-Out (ΔWZY) *Shigella* Strains

Each of the internal DNA fragments of wzy having a length of approximately 600 nt (from nucleotides 121 to 720 (600 nt) (SEQ ID NO: 1) in the case of *Shigella flexneri* 2a; from nucleotides 5,027 to 5,672 (646 nt) (SEQ ID NO: 2) in the case of *Shigella flexneri* 6; from nucleotides 1,936 to 2,525 (590 nt) (SEQ ID NO: 3) in the case of *Shigella dysenteriae* 2; from nucleotides 5,207 to 5,796 (590 nt) (SEQ ID NO: 4) in the case of *Shigella sonnei* 482-79 (pWR105); and from nucleotides 9,161 to 9,799 (639 nt) (SEQ ID NO: 5) in the case of *Shigella boydii* 7) was amplified by PCR using forward and reverse primers as listed in Table 1 (C. Daniels, C. Vindurampulle, R. Morona, Overexpression and topology of the *Shigella flexneri* O-antigen polymerase (Rfc/Wzy), Mol Microbiol 28 (1998) 1211-1222).

TABLE 1

Nucleotide sequences of primers used in PCR cloning of internal 600 nt DNA fragments of WZY

| WZY | Primers | Nucleotide sequences | SEQ ID NO |
|---|---|---|---|
| *S. flexneri* 2a | Forward | 5'-GGCTCTAGAAGTTTTATACTTTTAATTTTTAATTTAGTT-3' | 8 |
| | Reverse | 5'-GCCGAATTCAAATAGAACGCTGCCCAATA-3' | 9 |
| *S. flexneri* 6 | Forward | 5'-TCATTTTCTAGAAAAATTGCAAACGGAAT-3' | 10 |
| | Reverse | 5'-AAGAAGGAATTCCTCCATTTGATTTCATGATT-3' | 11 |
| *S. dysenteriae* 2 | Forward | 5'-TTTTATTCTAGAGGATTCTTTCCTGCCCCATA-3' | 12 |
| | Reverse | 5'-AATTTTGAATTCACATCAACTTTCATGCCACA-3' | 13 |
| *S. sonnei* 482-79 (pWR105) | Forward | 5'-GATTCTAGACGTTGAGGTTTCACGTTTCTC-3' | 14 |
| | Reverse | 5'-AACGAATTCCGAAGACAGCATTCGTTCAA-3' | 15 |
| *S. boydii* 7 | Forward | 5'-GGCTCTAGATCCCATTGGTTCAATTCTTT-3' | 16 |
| | Reverse | 5'-CCGGAATTCTTAGCTAACAAAACGTGCTCA-3' | 17 |

In the primer sequences, the underlined parts represent XbaI and EcoRI restriction sites, respectively.

The PCR fragment was cloned into a pGEM-T vector system (Promega), digested with XbaI and EcoRI enzymes, and then inserted into a suicide plasmid pSW23.oriT (D. W. Kim, G. Lenzen, A. L. Page, P. Legrain, P. J. Sansonetti, C. Parsot, The *Shigella flexneri* effector OspG interferes with innate immune responses by targeting ubiquitin-conjugating enzymes, Proc Natl Acad Sci USA 102 (2005) 14046-14051). An *E. coli* strain BW19610 ($pir^+$ $Amp^s$ $Cm^r$) was transformed with each recombinant plasmid pSWwzyTr using a heat shock method. The wzy fragment of the recombinant plasmid pSWwzyTr was verified by nucleotide sequencing. The plasmid pSWwzyTr was purified from BW19610 using a Qiagen mini-prep kit, and *E. coli* SM10λpir ($pir^+$ $Tra^+$ $Amp^s$ $Cm^r$) was transformed with the purified plasmid pSWwzyTr using the heat shock method. The wzy fragment of the recombinant plasmid pSWwzyTr was verified by nucleotide sequencing. The plasmid pSWwzyTr was purified from BW19610 using a Qiagen mini-prep kit, and *E. coli* SM10λpir ($pir^+$ $Tra^+$ $Amp^s$ $Cm^r$) was transformed with the purified plasmid pSWwzyTr using the heat shock method. *E. coli* SM10λpir was conjugated with streptomycin-resistant *Shigella* and *Shigella* resistant to both streptomycin and chloramphenicol resistant, and the conjugated *Shigella* colonies were then isolated on a Congo Red/streptomycin/chloramphenicol agar plate (D. W. Kim, et al., Proc Natl Acad Sci USA 102 (2005) 14046-14051). Thereafter, the purified LPSs derived from the wild-type *Shigella* and ΔWZY were analysed by 14% Tris/Tricine SDS PAGE (30 ng/lane: 16.5% gel and 100 ng/lane in the case of *Shigella flexneri* 2a WT and ΔWZY) and silver staining.

Figure 2:
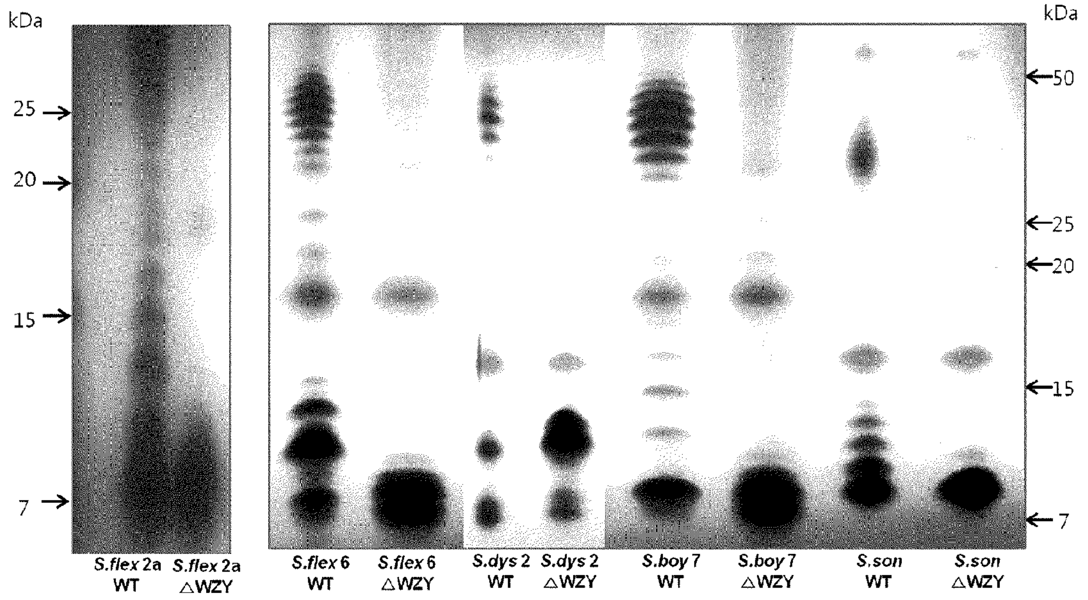
FIG. 2 shows results of lipopolyssacharide (LPS) analysis using silver staining. LPSs derived from the wild-type

As a result, it was confirmed that the ladder pattern specific to LPS (O-antigen polymerization) was observed from the wild types, but such a pattern disappeared in ΔWZY (FIG. 2).

Example 2: Culture of ΔWZY Strains

The ΔWZY strain was cultured from aliquots (frozen at −70° C. in 80% glycerin) overnight at 37° C. on a BTCS agar supplemented with 0.01% Congo red and 100 mg/mL of streptomycin (*Shigella flexneri* 2a ΔWZY); 20 mg/mL of ampicillin and 10 mg/mL of chloramphenicol (*Shigella flexneri* 6 ΔWZY); 50 mg/mL of streptomycin and 10 mg/mL of chloramphenicol (*Shigella* dysentriae 2 ΔWZY and *Shigella sonnei* ΔWZY); or 25 mg/mL of streptomycin and 10 mg/mL of chloramphenicol (*Shigella boydii* 7 ΔWZY) as the antibiotic(s). One representative Congo Red-stained colony was cultured overnight at 37° C. while stirring in a BTCS broth containing 100 mg/mL of streptomycin. Next morning, aliquots of ΔWZY (1 to 2% volume of a fresh medium) were added to a fresh BTCS broth containing an appropriate antibiotic(s) for each strain as described above, and cultured at 37° C. for 2 to 3 hours. After the OD was measured at 600 nm (an OD value of 0.5 was determined as an amount of $2\times10^8$ cfu/mL), the ΔWZY culture broth was centrifuged, and the bacterial pellets were suspended in PBS to a concentration of $5\times10^9$ cfu/mL.

Example 3: Immunization and Challenge of Mice

40 μL of PBS containing $1\times10^8$ cfu of ΔWZY was administered to Balb/c mice (female, 6 weeks old) via an intranasal route three times at intervals of two weeks. Bacteria were inactivated with 0.13% formalin/PBS (v/v) for 2 hours. SC602-immunized mice were used as the control (P. J. Sansonetti, Infect Agents Dis 2 (1993) 201-206). Only PBS was administered to the age- and gender-matched control mice. One week after the last immunization, the mice were challenged with infectious live *Shigella dysenteriae* 1, *Shigella flexneri* 2a 2457T, *Shigella flexneri* 6, *Shigella sonnei* through the intranasal route. The strains used for challenge were prepared and cultured in the same manner as in the ΔWZY strain. The survival of the mice was monitored daily for 7 to 10 days.

As a result, it was revealed that the intranasal administration of the ΔWZY strain provided partial or complete protection against experimental pneumonia induced by the strains belonging to the different *Shigella* species (*S. flexneri* and *S. dysenteriae*) and the different *Shigella* serotypes (*S. flexneri* 2a and 6). The results of the experiments are summarized in Table 2 and shown in FIGS. 3A to 6B.

TABLE 2

Survival rates of mice immunized with ΔWZY

| Challenge strain | Challenge dose/mouse | Group | No. of mice | Survival rate (%) |
|---|---|---|---|---|
| *S. flexneri* 2a | $1\times10^7$ cfu | Naive | n = 5 | 0 |
| | | WZY | n = 6 | 100 |
| *S. flexneri* 6 | $1\times10^7$ cfu | Naive | n = 6 | 16.7 |
| | | WZY | n = 6 | 100 |
| *S. dysenteriae* | $5\times10^6$ cfu | Naive | n = 5 | 0 |
| | | WZY | n = 5 | 80 |

Example 4: Flow Cytometric Analysis of Whole Cells by Several Kinds of Polyclonal Sera The equivalent number (approximately $2\times10^7$ cfu) of the freshly cultured *Shigella* wild type and ΔWZY thereof were used to stain surfaces of the whole cells with an anti-IcsP mouse polyclonal serum. The strain was inactivated with 0.13% formalin or PBS (v/v) for 2 hours. The whole cells were washed with PBS, and stained with a diluted solution from the antigen-specific mice. After the resulting samples were washed three times with PBS, an anti-mouse goat IgG-RPE antibody was added to the samples. The cells were washed with PBS, and then analyzed by flow cytometry.

Anti-serum against PSSP-1 as partial IcsP was developed by immunizing the mice 3 to 4 times with co-administration with dmLT (E. B. Norton, et al., Clin Vaccine Immunol 18 (2011) 546-551; J. O. Kim, et al., Clin Vaccine Immunol 22 (2015) 381-388). Naive mouse serum was used as the control.

As a result, it was confirmed that a larger amount of IcsP was detected in ΔWZY, compared to the wild-type *Shigella*, and that the outer membrane protein, IcsP, was buried by O-polysaccharides in the wild-type strain but easily detected on a surface of the ΔWZY due to a shorter length of one unit O-antigen (FIGS. 7A to 7E).

All the documents cited in this specification are included in this specification although it seems to show that the individual documents are specifically and separately encompassed by the citations. The foregoing invention is provided for the purpose of clarity in understanding, and is partially described in detail with reference to the examples. Therefore, it will be apparent to those skilled in the art on the basis of the contents disclosed in the present invention that some changes and modifications may be made to the examples without departing from the spirit and scope of the appended claims.

The invention claimed is:

1. A *Shigella* strain in which surface exposure of a protective antigen existing on a cellular membrane increases due to the deletion of wzy gene of *Shigella* species, wherein the protective antigen is an IcsP2 or SigA2 protein.

2. The *Shigella* strain of claim 1, wherein the wzy gene has a base sequence selected from the group consisting of SEQ ID NOs: 1 to 5.

3. The *Shigella* strain of claim 1, wherein the IcsP2 protein has an amino acid sequence of SEQ ID NO: 6.

4. The *Shigella* strain of claim 1, wherein the SigA2 protein has an amino acid sequence of SEQ ID NO: 7.

5. The *Shigella* strain of claim 1, wherein the *Shigella* species is selected from the group consisting of *Shigella dysenteriae, Shigella flexneri, Shigella boydii*, and *Shigella sonnei.*

6. The *Shigella* strain of claim 1, wherein the *Shigella* species is selected from the group consisting of *Shigella dysenteriae* type 1, *Shigella dysenteriae* 2, *Shigella flexneri* 2a, *Shigella flexneri* 3a, *Shigella flexneri* 5a, *Shigella flexneri* 5b, *Shigella flexneri* 6, *Shigella boydii* serotype 4, *Shigella boydii* 7, and *Shigella sonnei* 482-79.

7. A vaccine composition for treating or preventing shigellosis, comprising the *Shigella* strain according to claim 1 and an adjuvant.

8. The vaccine composition of claim 7, wherein the *Shigella* strain is selected from the group consisting of an attenuated strain, a live strain, and a dead strain.

9. The vaccine composition of claim 7, wherein the adjuvant is selected from the group consisting of an aluminum salt, an immune stimulating complex (ISCOM), a saponin-based adjuvant, an oil-in-water emulsion, a water-in-oil emulsion, a toll-like receptor ligand such as a muramyl dipeptide, *Escherichia coli* (*E. coli*) LPS, an oligonucleotide containing unmethylated DNA, poly(I:C), lipoteichoic acid, a peptidoglycan, a cholera toxin, a heat-labile *E. coli* enterotoxin, a pertussis toxin, and a Shiga toxin.

10. The vaccine composition of claim 7, wherein an effective dose of the vaccine composition is in a range of 10 μg to 2 mg.

* * * * *